(12) United States Patent
Moses et al.

(10) Patent No.: US 7,252,667 B2
(45) Date of Patent: Aug. 7, 2007

(54) OPEN VESSEL SEALING INSTRUMENT WITH CUTTING MECHANISM AND DISTAL LOCKOUT

(75) Inventors: Michael C. Moses, Boulder, CO (US); Paul R. Romero, Loveland, CO (US); Kristin D. Johnson, Louisville, CO (US); Duane E. Kerr, Berthoud, CO (US); Sean T. Dycus, Denver, CO (US)

(73) Assignee: Sherwood Services AG, Schaffenhausen (CH)

( * ) Notice: Subject to any disclaimer, the term of this patent is extended or adjusted under 35 U.S.C. 154(b) by 409 days.

(21) Appl. No.: 10/873,860

(22) Filed: Jun. 22, 2004

(65) Prior Publication Data
US 2005/0107784 A1    May 19, 2005

Related U.S. Application Data

(63) Continuation-in-part of application No. 10/991,157, filed on Nov. 17, 2004.

(60) Provisional application No. 60/523,387, filed on Nov. 19, 2003, now Pat. No. 7,131,970.

(51) Int. Cl.
*A61B 18/18* (2006.01)

(52) U.S. Cl. .......................... 606/51; 606/1

(58) Field of Classification Search ............ 606/40–42, 606/50–52, 1
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,588,645 A | 6/1926 | Bierman |
| 2,002,594 A | 5/1935 | Wappler et al. |

(Continued)

FOREIGN PATENT DOCUMENTS

CA    2104423    2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Michael Peffley
*Assistant Examiner*—Pete Vrettakos

(57) ABSTRACT

An open electrosurgical forceps for sealing tissue includes a pair of first and second shaft members each having a jaw member disposed at a distal end thereof. The jaw members are movable from a first position in spaced relation relative to one another to a subsequent position wherein the jaw members cooperate to grasp tissue therebetween. Each of the jaw members includes an electrically conductive sealing plate for communicating electrosurgical energy through tissue held therebetween. At least one of the jaw members includes a knife channel defined along a length thereof which is dimensioned to reciprocate a cutting mechanism therealong for cutting tissue disposed between jaw members. An actuator having a rack and pinion system advances the cutting mechanism from a first position wherein the cutting mechanism is disposed proximal to tissue held between the jaw members to at least one subsequent position wherein the cutting mechanism is disposed distal to tissue held between the jaw members.

12 Claims, 14 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,068,721 A | 1/1937 | Wappler et al. |
| 2,176,479 A | 10/1939 | Willis |
| 2,305,156 A | 12/1942 | Grubel |
| 2,315,328 A | 3/1943 | Gmeiner |
| 2,632,661 A | 3/1953 | Cristofv |
| 2,668,538 A | 2/1954 | Baker |
| 2,676,406 A | 4/1954 | Hoke |
| 2,679,249 A | 5/1954 | Weihmann |
| 2,796,065 A | 6/1957 | Kapp |
| 2,853,074 A | 9/1958 | Olson |
| 3,175,556 A | 3/1965 | Wood et al. |
| 3,443,313 A | 5/1969 | Profy |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,041,952 A | 8/1977 | Morrison, Jr. et al. |
| 4,074,718 A | 2/1978 | Morrison, Jr. |
| 4,088,134 A | 5/1978 | Mazzariello |
| 4,128,099 A | 12/1978 | Bauer |
| 4,165,746 A | 8/1979 | Burgin |
| 4,271,838 A | 6/1981 | Lasner et al. |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,214 A | 7/1990 | Specht et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,356 A | 9/1992 | Bhatta |
| 5,147,357 A | 9/1992 | Rose et al. |
| 5,151,102 A | 9/1992 | Xamiyama et al. |
| 5,176,695 A | 1/1993 | Dulebohn |
| 5,176,696 A | 1/1993 | Saunders |
| 5,190,541 A | 3/1993 | Abele et al. |
| 5,196,009 A | 3/1993 | Kirwan, Jr. |
| 5,196,023 A | 3/1993 | Martin |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,817 A | 2/1994 | Hoogeboom et al. |
| 5,290,286 A | 3/1994 | Parins |
| 5,290,287 A | 3/1994 | Boebel et al. |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,331,971 A | 7/1994 | Bales et al. |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,423,841 A | 6/1995 | Kornefeld |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |

| | | | | | |
|---|---|---|---|---|---|
| 5,542,945 A | 8/1996 | Fritzsch | 5,843,080 A | 12/1998 | Fleenor et al. |
| 5,554,164 A | 9/1996 | Wilson et al. | 5,849,022 A | 12/1998 | Sakashita et al. |
| 5,558,672 A | 9/1996 | Edwards et al. | 5,853,412 A | 12/1998 | Mayenberger |
| 5,562,694 A | 10/1996 | Sauer et al. | 5,860,976 A | 1/1999 | Billings et al. |
| 5,562,699 A | 10/1996 | Heimberger et al. | 5,876,401 A | 3/1999 | Schulze et al. |
| 5,569,241 A | 10/1996 | Edwardds | 5,891,141 A | 4/1999 | Rydell |
| 5,569,243 A | 10/1996 | Kortenbach et al. | 5,891,142 A | 4/1999 | Eggers et al. |
| 5,571,100 A | 11/1996 | Goble et al. | 5,893,863 A | 4/1999 | Yoon |
| 5,573,424 A | 11/1996 | Poppe | 5,893,875 A | 4/1999 | O'Connor et al. |
| 5,573,534 A | 11/1996 | Stone | 5,893,877 A | 4/1999 | Gampp, Jr. et al. |
| 5,573,535 A | 11/1996 | Viklund | 5,902,301 A | 5/1999 | Olig |
| 5,582,611 A | 12/1996 | Tsukagoshi et al. | 5,906,630 A | 5/1999 | Anderhub et al. |
| 5,585,896 A | 12/1996 | Yamazaki et al. | 5,908,420 A | 6/1999 | Parins et al. |
| 5,590,570 A | 1/1997 | LeMaire, III et al. | 5,911,719 A | 6/1999 | Eggers |
| 5,601,601 A | 2/1997 | Tal et al. | 5,913,874 A | 6/1999 | Berns et al. |
| 5,603,711 A | 2/1997 | Parins et al. | 5,921,984 A | 7/1999 | Sutcu et al. |
| 5,603,723 A | 2/1997 | Aranyi et al. | 5,925,043 A | 7/1999 | Kumar et al. |
| 5,611,798 A | 3/1997 | Eggers | 5,935,126 A | 8/1999 | Riza |
| 5,626,578 A | 5/1997 | Tihon | 5,944,718 A | 8/1999 | Dafforn et al. |
| 5,626,609 A | 5/1997 | Zvenyatsky et al. | 5,951,549 A | 9/1999 | Richardson et al. |
| 5,630,833 A | 5/1997 | Katsaros et al. | 5,954,720 A | 9/1999 | Wilson et al. |
| 5,637,110 A | 6/1997 | Pennybacker et al. | 5,957,923 A | 9/1999 | Hahnen et al. |
| 5,643,294 A | 7/1997 | Tovey et al. | 5,961,514 A | 10/1999 | Long et al. |
| 5,647,869 A | 7/1997 | Goble et al. | 5,976,132 A | 11/1999 | Morris |
| 5,647,871 A | 7/1997 | Levine et al. | 5,984,939 A | 11/1999 | Yoon |
| 5,649,959 A | 7/1997 | Hannam et al. | 5,989,277 A | 11/1999 | LeMaire, III et al. |
| 5,658,281 A | 8/1997 | Heard | 6,004,335 A | 12/1999 | Vaitekunas et al. |
| 5,662,667 A | 9/1997 | Knodel | 6,010,516 A | 1/2000 | Hulka |
| 5,665,100 A | 9/1997 | Yoon | 6,024,741 A * | 2/2000 | Williamson et al. .......... 606/40 |
| 5,667,526 A | 9/1997 | Levin | 6,024,744 A | 2/2000 | Kese et al. |
| 5,674,220 A | 10/1997 | Fox et al. | 6,033,399 A | 3/2000 | Gines |
| 5,681,282 A | 10/1997 | Eggers et al. | 6,039,733 A | 3/2000 | Buysse et al. |
| 5,693,051 A | 12/1997 | Schulze et al. | 6,041,679 A | 3/2000 | Slater et al. |
| 5,695,511 A | 12/1997 | Cano et al. | 6,050,996 A | 4/2000 | Schmaltz et al. |
| 5,695,522 A | 12/1997 | LeMaire, III et al. | 6,053,914 A | 4/2000 | Eggers et al. |
| 5,700,261 A | 12/1997 | Brinkerhoff | 6,053,933 A | 4/2000 | Balazs et al. |
| 5,702,390 A | 12/1997 | Austin et al. | D424,694 S | 5/2000 | Tetzlaff et al. |
| 5,707,369 A | 1/1998 | Vaitekunas et al. | D425,201 S | 5/2000 | Tetzlaff et al. |
| 5,709,680 A | 1/1998 | Yates et al. | 6,059,782 A | 5/2000 | Novak et al. |
| 5,716,366 A | 2/1998 | Yates | RE36,795 E | 7/2000 | Rydell |
| 5,720,744 A | 2/1998 | Eggleston et al. | 6,083,223 A | 7/2000 | Baker |
| 5,727,428 A | 3/1998 | LeMaire, III et al. | 6,086,586 A | 7/2000 | Hooven |
| 5,730,750 A | 3/1998 | Haradon | 6,090,107 A | 7/2000 | Borgmeier et al. |
| 5,735,848 A | 4/1998 | Yates et al. | 6,096,031 A | 8/2000 | Mitchell et al. |
| 5,743,906 A | 4/1998 | Parins et al. | 6,096,037 A | 8/2000 | Mulier et al. |
| 5,749,893 A | 5/1998 | Vidal et al. | 6,099,550 A | 8/2000 | Yoon |
| 5,755,717 A | 5/1998 | Yates et al. | 6,102,909 A | 8/2000 | Chen et al. |
| 5,766,130 A | 6/1998 | Selmonosky | 6,110,171 A | 8/2000 | Rydell |
| 5,766,166 A | 6/1998 | Hooven | 6,113,596 A | 9/2000 | Hooven et al. |
| 5,766,170 A | 6/1998 | Eggers | 6,113,598 A | 9/2000 | Baker |
| 5,769,849 A | 6/1998 | Eggers | 6,117,158 A | 9/2000 | Measamer et al. |
| 5,772,655 A | 6/1998 | Bauer et al. | 6,123,701 A | 9/2000 | Nezhat |
| 5,772,670 A | 6/1998 | Brosa | H1904 H | 10/2000 | Yates et al. |
| 5,776,128 A | 7/1998 | Eggers | 6,126,658 A | 10/2000 | Baker |
| 5,776,130 A | 7/1998 | Buysse et al. | 6,146,399 A | 11/2000 | Lee |
| 5,779,701 A | 7/1998 | McBrayer et al. | 6,152,923 A | 11/2000 | Ryan |
| 5,792,137 A | 8/1998 | Carr et al. | 6,174,309 B1 | 1/2001 | Wrublewski et al. |
| 5,792,177 A | 8/1998 | Kaseda | 6,179,834 B1 | 1/2001 | Buysse et al. |
| 5,797,936 A | 8/1998 | Kleihues | 6,179,837 B1 | 1/2001 | Hooven |
| 5,797,938 A | 8/1998 | Paraschac et al. | 6,183,467 B1 | 2/2001 | Shapeton et al. |
| 5,797,958 A | 8/1998 | Yoon | 6,187,003 B1 | 2/2001 | Buysse et al. |
| 5,800,449 A | 9/1998 | Wales | 6,190,386 B1 | 2/2001 | Rydell |
| 5,807,393 A | 9/1998 | Williamson, IV et al. | 6,193,718 B1 | 2/2001 | Kortenbach et al. |
| 5,810,808 A | 9/1998 | Eggers | 6,206,876 B1 | 3/2001 | Levine et al. |
| 5,810,811 A | 9/1998 | Yates et al. | 6,206,877 B1 | 3/2001 | Kese et al. |
| 5,810,877 A | 9/1998 | Roth et al. | 6,217,602 B1 | 4/2001 | Redmon |
| 5,814,043 A | 9/1998 | Shapeton | 6,224,593 B1 | 5/2001 | Ryan et al. |
| 5,817,093 A | 10/1998 | Williamson, IV et al. | 6,228,080 B1 | 5/2001 | Gines |
| 5,820,630 A | 10/1998 | Lind | 6,228,083 B1 | 5/2001 | Lands et al. |
| 5,827,271 A | 10/1998 | Buysse et al. | 6,267,761 B1 | 7/2001 | Ryan |
| 5,827,279 A | 10/1998 | Hughett et al. | 6,270,497 B1 | 8/2001 | Sekino et al. |
| 5,827,281 A | 10/1998 | Levin | 6,270,508 B1 | 8/2001 | Klieman et al. |
| 5,833,690 A | 11/1998 | Yates et al. | 6,273,887 B1 | 8/2001 | Yamauchi et al. |

| | | |
|---|---|---|
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,322,561 B1 | 11/2001 | Eggers et al. |
| 6,334,860 B1 | 1/2002 | Dorn |
| 6,334,861 B1 | 1/2002 | Chandler et al. |
| 6,350,264 B1 | 2/2002 | Hooven |
| 6,352,536 B1 | 3/2002 | Buysse et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,701 B1 | 10/2002 | Hooven et al. |
| 6,464,704 B2 | 10/2002 | Schmaltz et al. |
| 6,478,794 B1 | 11/2002 | Trapp et al. |
| 6,503,248 B1 | 1/2003 | Levine |
| 6,506,189 B1 | 1/2003 | Rittman, III et al. |
| 6,508,815 B1 | 1/2003 | Strul et al. |
| 6,511,480 B1 | 1/2003 | Tetzlaff et al. |
| 6,514,251 B1 | 2/2003 | Ni et al. |
| 6,544,264 B2 | 4/2003 | Levine et al. |
| 6,569,162 B2 | 5/2003 | He |
| 6,585,735 B1 | 7/2003 | Frazier et al. |
| 6,620,161 B2 | 9/2003 | Schulze et al. |
| 6,652,521 B2 | 11/2003 | Schulze |
| 6,656,177 B2 | 12/2003 | Truckai et al. |
| 6,669,696 B2 | 12/2003 | Bacher et al. |
| 6,679,882 B1 | 1/2004 | Kornerup |
| 6,682,528 B2 | 1/2004 | Frazier et al. |
| 6,685,724 B1 | 2/2004 | Haluck |
| 6,733,498 B2 | 5/2004 | Paton et al. |
| 6,743,229 B2 | 6/2004 | Buysse et al. |
| 6,770,072 B1 | 8/2004 | Truckai et al. |
| 6,773,434 B2 | 8/2004 | Ciarrocca |
| 6,776,780 B2 | 8/2004 | Mulier et al. |
| D496,997 S | 10/2004 | Dycus et al. |
| 6,802,843 B2 | 10/2004 | Truckai et al. |
| D499,181 S | 11/2004 | Dycus et al. |
| 6,818,000 B2 | 11/2004 | Muller et al. |
| 6,926,716 B2 | 8/2005 | Baker et al. |
| 6,929,644 B2 | 8/2005 | Truckai et al. |
| 6,932,810 B2 | 8/2005 | Ryan |
| 6,942,662 B2 | 9/2005 | Goble et al. |
| 6,964,662 B2 | 11/2005 | Kidooka |
| 7,033,354 B2 | 4/2006 | Keppel |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,118,570 B2 | 10/2006 | Tetzlaff et al. |
| 7,118,587 B2 | 10/2006 | Dycus et al. |
| 2002/0013583 A1 | 1/2002 | Camran et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0018331 A1 | 1/2003 | Dycus et al. |
| 2003/0069571 A1 | 4/2003 | Treat et al. |
| 2003/0078578 A1 | 4/2003 | Csaba et al |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0116979 A1 | 6/2004 | Truckai et al. |
| 2004/0147925 A1 | 7/2004 | Buysse et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149151 A1 | 7/2005 | Orszulak et al. |
| 2006/0064085 A1 | 3/2006 | Schechter et al. |
| 2006/0079891 A1 | 4/2006 | Arts et al. |
| 2006/0129148 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |

FOREIGN PATENT DOCUMENTS

| | | |
|---|---|---|
| DE | 2415263 | 10/1975 |
| DE | 8712328 | 3/1988 |
| DE | 29616210 | 1/1997 |
| DE | 19608716 | 4/1997 |
| DE | 19751108 | 5/1999 |
| EP | 0364216 A1 | 4/1990 |
| EP | 0518230 A1 | 12/1992 |
| EP | 0 541 930 B1 | 5/1993 |
| EP | 0572131 | 12/1993 |
| EP | 0584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0853922 A1 | 7/1998 |
| EP | 0875209 A1 | 11/1998 |
| EP | 0878169 A1 | 11/1998 |
| EP | 0887046 A3 | 1/1999 |

| | | |
|---|---|---|
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1330991 A1 | 7/2003 |
| EP | 1488177 A2 | 6/2004 |
| EP | 1532932 A1 | 5/2005 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| RU | 197711 | 8/1967 |
| RU | 401367 | 11/1974 |
| WO | WO 92/06642 | 4/1992 |
| WO | WO 94/08524 A | 4/1994 |
| WO | WO 95/02369 | 1/1995 |
| WO | WO 95/07662 | 3/1995 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 A | 3/1999 |
| WO | WO 99/40857 | 8/1999 |
| WO | WO 99/040861 | 8/1999 |
| WO | WO 99/51158 | 10/1999 |
| WO | WO 99/066850 | 12/1999 |
| WO | WO 99/66850 A | 12/1999 |
| WO | WO 00/24330 | 5/2000 |
| WO | WO 00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080796 A1 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/01311 | 12/2003 |
| WO | WO 04/032777 | 4/2004 |
| WO | WO 2004/052221 A1 | 6/2004 |
| WO | WO 04/073490 | 9/2004 |
| WO | WO 04/082495 | 9/2004 |
| WO | WO 2004/082495 A1 | 9/2004 |
| WO | WO 2004/098383 A1 | 11/2004 |
| WO | WO 04/103156 | 12/2004 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Saytan et al. "Sutureless Closed Hemorrhoidectomy: A New Technique" Annals of Surgery vol. 234 No. 1 Jul. 2001 pp. 21-24.

Haniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10-77.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature.

LigaSure Vessel Sealing System, the Seal of Confidence in General, Gynecologic, Urologic, and Laparaoscopic Surgery Sales/Product Literature.

Carbonell et al., "Comparison of theGyrus PlasmaKinetic Sealer and the Valleytab LigaSure Device in the Hemostasis of Small, Medium, and Large-Sized Arteries" Carolinas Laparoscopic and Advanced Surgery Program, Carolinas Medical Center, Charlotte, NC.

"Reducing Needlestick Injuries in the Operating Room" Sales/Product Literature.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 8, No. 4, Jul./Aug. 2002 pp. 569-574.

Paul G. Horgan, "A Novel Technique for Parenchymal Division During Hepatectomy" The American Journal of Surgery, vol. 181, No. 3, □Apr. 2001 pp. 236-237.

W. Scott Helton, "LigaSure Vessel Sealing System: Revolutionary Hemostasis Product for General Surgery" Sales/Product Literature.

Michael Choti, "Abdominoperineal Resection with the LigaSure Vessel Sealing system and LigaSure Atlas 20 cm Open Instrument" Innovations That Work, □Jun. 2003.

Craig Johnson, "Use of the LigaSure Vessel Sealing System in Bloodless Hemorrhoidectomy" Innovations That Work,☐Mar. 2000.

Muller et al., "Extended Left Hemicolectomy Using the LigaSure Vessel Sealing System" Innovations That Work,☐Sep. 1999.

Herman et al., "Laparoscopic Intestinal Resection With the LigaSure Vessel Sealing System: A Case Report" Innovations That Work,☐Feb. 2002.

Carus et al., "Initial Experience With The LigaSure Vessel Sealing System in Abdominal Surgery" Innovations That Work,☐Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature.

Sengupta et al., "Use of a Computer-Controlled Bipolar Diathermy System in Radical Prostatectomies and Other Open Urological Surgery" ANZ Journal of Surgery (2001) 71.9 pp 538-540.

Olsson et al. "Radical Cystectomy in Females" Current Surgical Techniques in Urology, vol. 14, Issue 3.

E. David Crawford "Use of a Novel Vessel Sealing Technology in Management of the Dorsal Velnous Complex" Sales/Product Literature.

Jarrett et al., "Use of the LigaSure Vessel Sealing System for Perl-Hilar Vessels in Laparoscopic Nephrectomy" Sales/Product Literature.

E. David Crawford "Evaluation of a New Vessel Sealing Device in Urologic Cancer Surgery" Sales/Product Literature.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature.

Johnson et al. "Evaluation of a Bipolar electrothermal Vessel Sealing Device in Hemorrhoidectomy" Sales/Product Literature.

Int'l Search Report PCT/US01/11218.
Int'l Search Report PCT/US99/24869.
Int'l Search Report PCT/US98/18640.
Int'l Search Report PCT/US98/23950.
PCT/US01/11340 International Search Report.
PCT/US01/11420 International Search Report.
PCT/US02/01890 International Search Report.
PCT/US02/11100 International Search Report.
PCT/US04/03436 International Search Report.
PCT/US04/13273 International Search Report.
PCT/US04/15311 International Search Report.
EP 98944778 International Search Report.
EP 98958575 International Search Report.
EP 04027479 International Search Report.
EP 04027705 International Search Report.
EP 04027314 International Search Report.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Olsson et al. "Radical Cystectomy in Females" Current Surgical Techniques in Urology, vol. 14, Issue 3, 2001.

Dulemba et al. "Use of a Bipolar Electrothermal Vessel Sealer in Laparoscopically Assisted Vaginal Hysterectomy" Sales Product Literature; Jan. 2004.

Johnson et al. "Evaluation of a Bipolar electrothermal Vessel Sealing Device in Hemorrhoidectomy" Sales Product Literature; Jan. 2004.

International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report —extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
US 6,663,629, 12/2003, Buysse et al. (withdrawn)

* cited by examiner

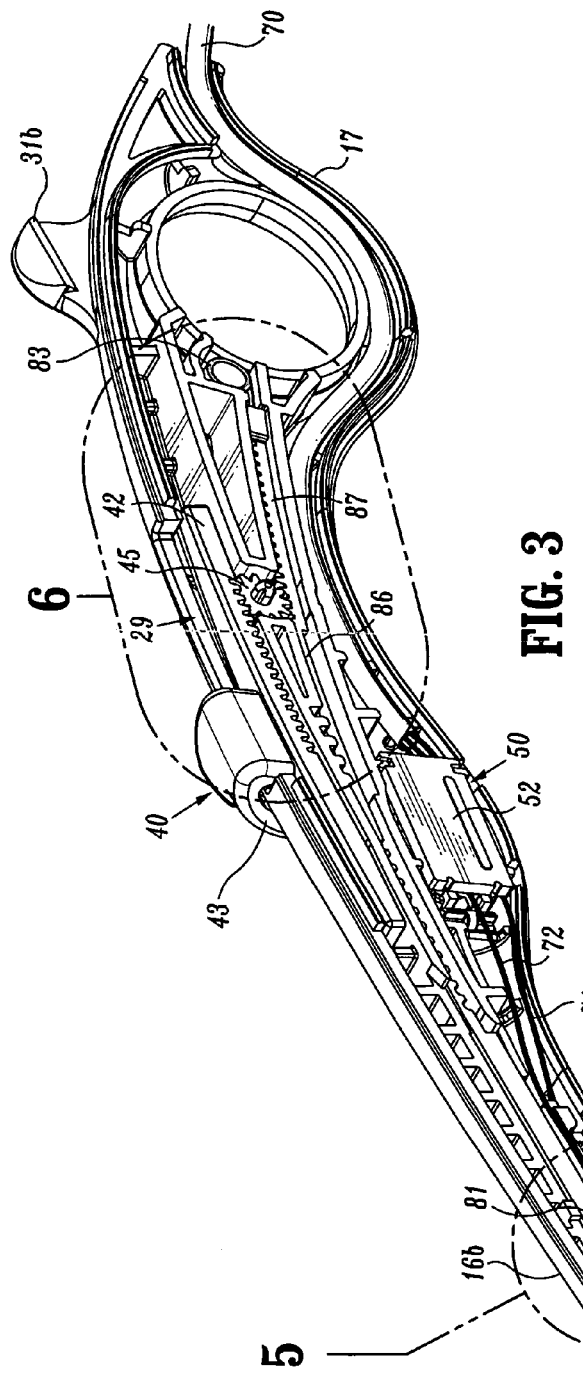
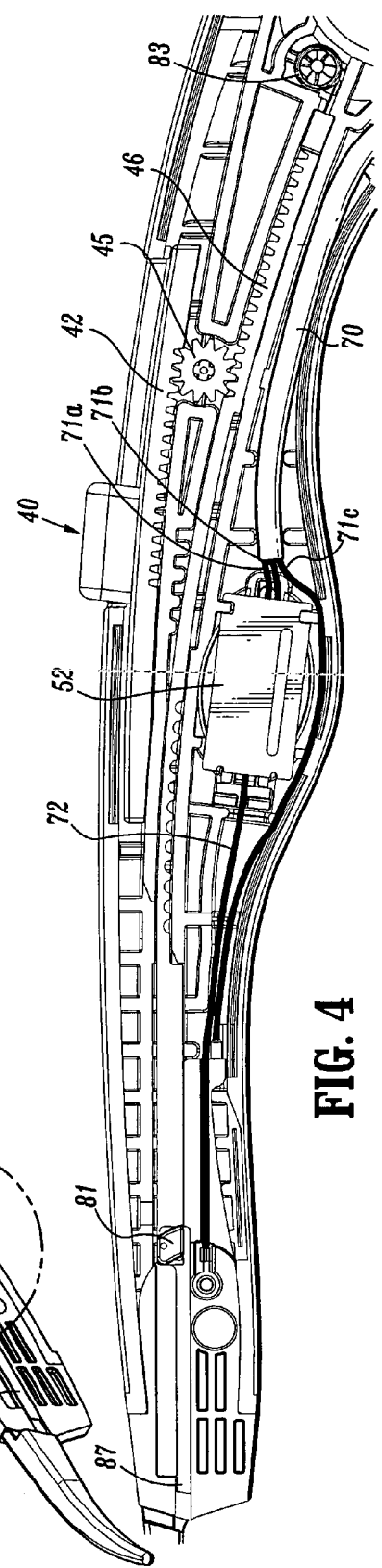
FIG. 3
FIG. 4

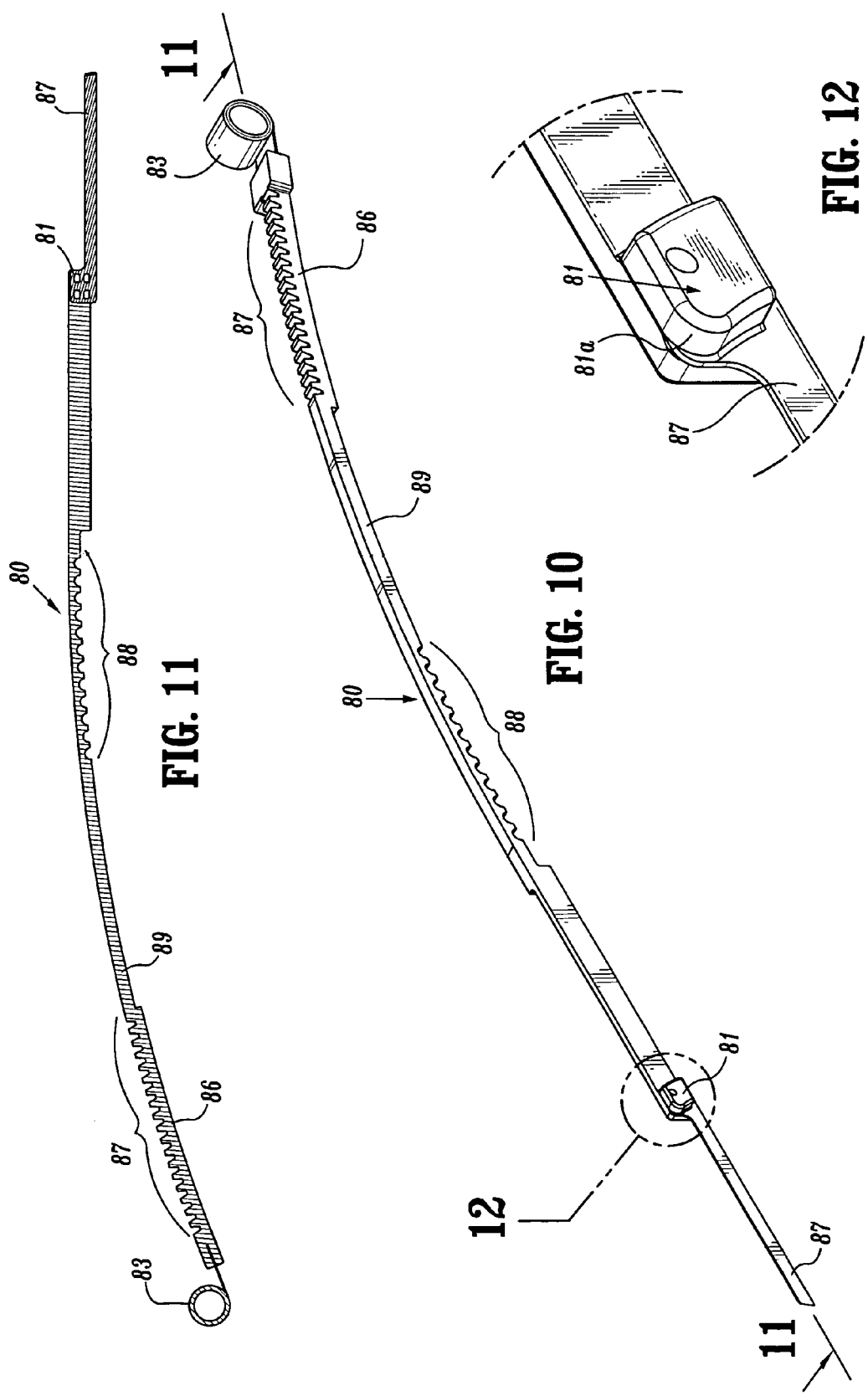

OPEN VESSEL SEALING INSTRUMENT WITH CUTTING MECHANISM AND DISTAL LOCKOUT

CROSS REFERENCE TO RELATED APPLICATION

The present application is a continuation-in-part of Ser. No. 10/991,157 filed on Nov. 17, 2004 and claims the benefit of priority to U.S. Provisional Application Ser. No. 60/523,387 (now U.S. Pat. No. 7,131,970) filed on Nov. 19, 2003 by Moses et al., the entire contents of which being incorporated by reference herein.

BACKGROUND

The present disclosure relates to forceps used for open surgical procedures. More particularly, the present disclosure relates to an open forceps which applies a combination of mechanical clamping pressure and electrosurgical energy to seal tissue and a knife which is selectively advanceable to sever tissue along the tissue seal.

TECHNICAL FIELD

A forceps is a plier-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize both mechanical clamping action and electrical energy to effect hemostasis by heating tissue and blood vessels to coagulate and/or cauterize tissue.

Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Vessel sealing or tissue sealing is a recently-developed technology which utilizes a unique combination of radiofrequency energy, pressure and gap control to effectively seal or fuse tissue between two opposing jaw members or sealing plates. Vessel or tissue sealing is more than "cauterization" which involves the use of heat to destroy tissue (also called "diathermy" or "electrodiathermy"). Vessel sealing is also more than "coagulation" which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

In order to effectively "seal" tissue or vessels, two predominant mechanical parameters must be accurately controlled: 1) the pressure or closure force applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that a good seal for certain tissues is optimum between about 0.001 inches and about 0.006 inches.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Commonly owned, U.S. Pat. No. 6,511,480, PCT Patent Application Nos. PCT/US01/11420 and PCT/US01/11218, U.S. patent applications Ser. Nos. 10/116,824, 10/284,562 and 10/299,650 all describe various open surgical forceps which seal tissue and vessels. All of these references are hereby incorporated by reference herein. In addition, several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

Typically and particularly with respect to open electrosurgical procedures, once a vessel is sealed, the surgeon has to remove the sealing instrument from the operative site, substitute a new instrument and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Many endoscopic vessel sealing instruments have been designed which incorporate a knife or blade member which effectively severs the tissue after forming a tissue seal. For example, commonly-owned U.S. Application Ser. No. 10/116,944 (now U.S. Pat. No. 7,083,618) and Ser. No. 10/179,863 (now U.S. Pat. No. 7,101,371) describe one such endoscopic instrument which effectively seals and cuts tissue along the tissue seal. Other instruments include blade members or shearing members which simply cut tissue in a mechanical and/or electromechanical manner and are relatively ineffective for vessel sealing purposes.

There exists a need to develop an open electrosurgical forceps which is simple, reliable and inexpensive to manufacture and which effectively seals tissue and vessels and which allows a surgeon to utilize the same instrument to effectively sever the tissue along the newly formed tissue seal.

SUMMARY

The present disclosure relates to an open electrosurgical forceps for sealing tissue and includes a pair of first and second shaft members each having a jaw member disposed at a distal end thereof. The jaw members are movable from a first position in spaced relation relative to one another to at least one subsequent position wherein the jaw members cooperate to grasp tissue therebetween. Each of the jaw members includes an electrically conductive sealing plate or sealing surface on an inner facing surface which communicates electrosurgical energy through tissue held therebetween. Preferably, one of the jaw members includes a knife slot or knife channel defined along a longitudinal length thereof which is dimensioned to reciprocate a cutting mechanism therealong to sever tissue held between the jaw members. An actuator is included for selectively advancing the cutting mechanism from a first position wherein the cutting mechanism is disposed proximal to tissue held between the jaw members to at least one subsequent position wherein the cutting mechanism is disposed distal to tissue held between the jaw members.

Preferably, the actuator includes a trigger which cooperates with a rack and pinion system to advance the cutting mechanism from the first to second positions through tissue held therebetween. The rack and pinion system includes a first gear-like rack associated with the trigger; a second gear-like rack associated with the cutting mechanism; and a pinion disposed between the first and second racks. Preferably, the trigger of the actuator may be moved proximally, distally or laterally to distally advance the cutting mechanism through the knife channel. Advantageously, the rack and pinion system is disposed within one of the first and second shaft members.

In one embodiment, the forceps includes a safety mechanism or safety lockout to prevent reciprocation of the cutting mechanism when the jaw members are disposed in the first position. The safety lockout may form part of one or both of the jaw members and/or may be integrally associated with the cutting mechanism.

In another embodiment, the forceps includes one or more springs which automatically bias the cutting mechanism in the first position such that after the cutting mechanism severs the tissue held between the jaw members, the cutting mechanism automatically returns to the first position. Preferably, the cutting mechanism includes at least one spring for automatically returning the cutting mechanism back to the first position.

BRIEF DESCRIPTION OF THE DRAWINGS

Various embodiments of the subject instrument are described herein with reference to the drawings wherein:

FIG. 3 is an internal, perspective view of the forceps of FIG. 1 showing a rack and pinion actuating mechanism for advancing the cutting mechanism and a series of internally disposed electrical connections for energizing the forceps;

FIG. 4 is an internal, side view of the forceps showing the rack and pinion actuating mechanism and the internally disposed electrical connections;

FIG. 10 is an enlarged, perspective view of the cutting mechanism;

FIG. 11 is a side cross section along lines 11-11 of FIG. 10;

FIG. 12 is an enlarged, perspective view of the area of detail in FIG. 10;

DETAILED DESCRIPTION

Figure 1:
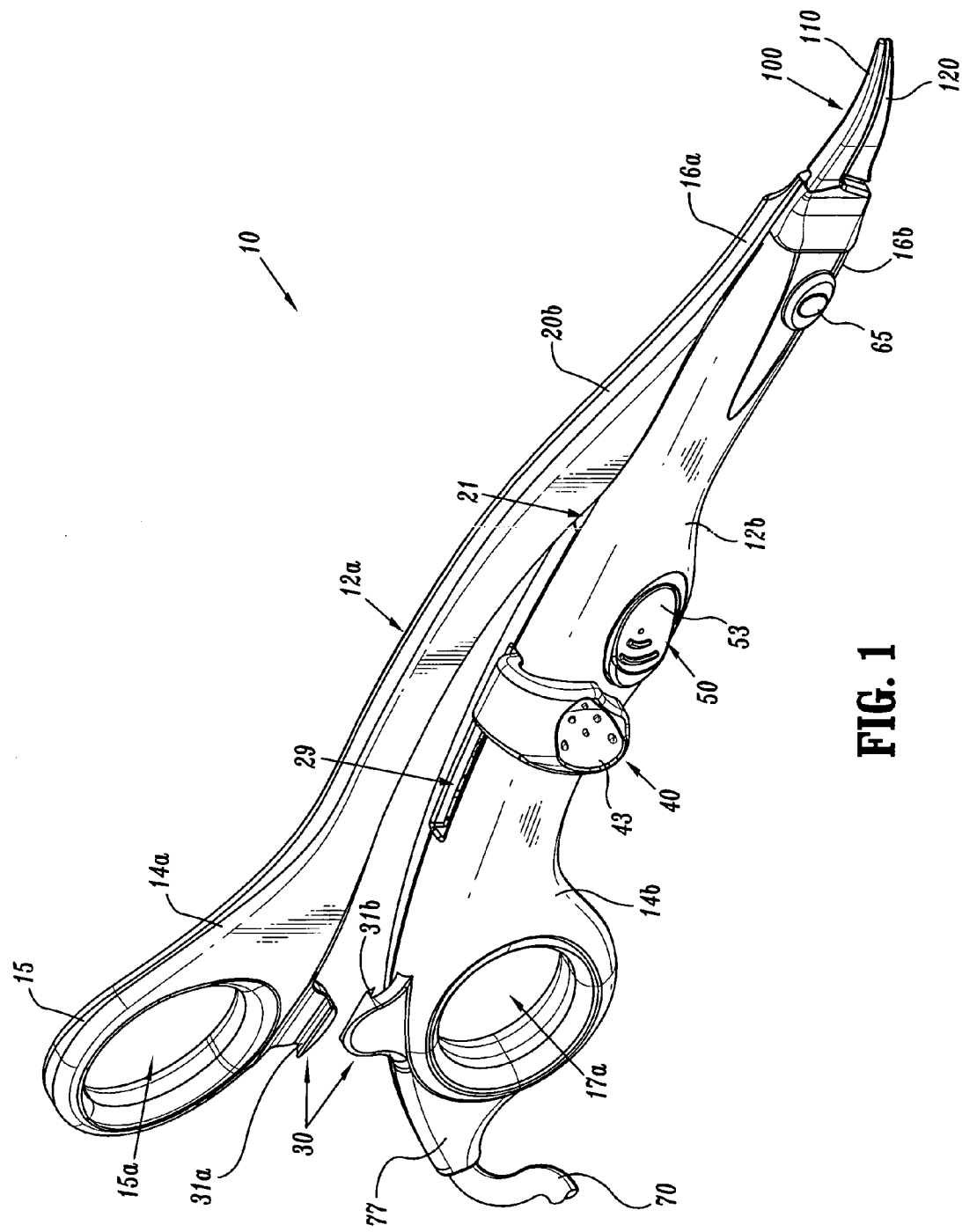
FIG. 1 is a left, perspective view of an open forceps with a cutting mechanism according to the present disclosure.

Referring now to FIGS. 1-7, a forceps 10 for use with open surgical procedures includes elongated shaft portions 12a and 12b each having a proximal end 14a, 14b and a distal end 16a and 16b, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 100 which attaches to the distal ends 16a and 16b of shafts 12a and 12b, respectively. As explained in more detail below, the end effector assembly 100 includes pair of opposing jaw members 110 and 120 which are pivotably connected about a pivot pin 65 and which are movable relative to one another to grasp tissue.

Preferably, each shaft 12a and 12b includes a handle 15 and 17, respectively, disposed at the proximal end 14a and 14b thereof which each define a finger hole 15a and 17a, respectively, therethrough for receiving a finger of the user. As can be appreciated, finger holes 15a and 17a facilitate movement of the shafts 12a and 12b relative to one another which, in turn, pivot the jaw members 110 and 120 from an open position wherein the jaw members 110 and 120 are disposed in spaced relation relative to one another to a clamping or closed position wherein the jaw members 110 and 120 cooperate to grasp tissue therebetween.

Figure 7:
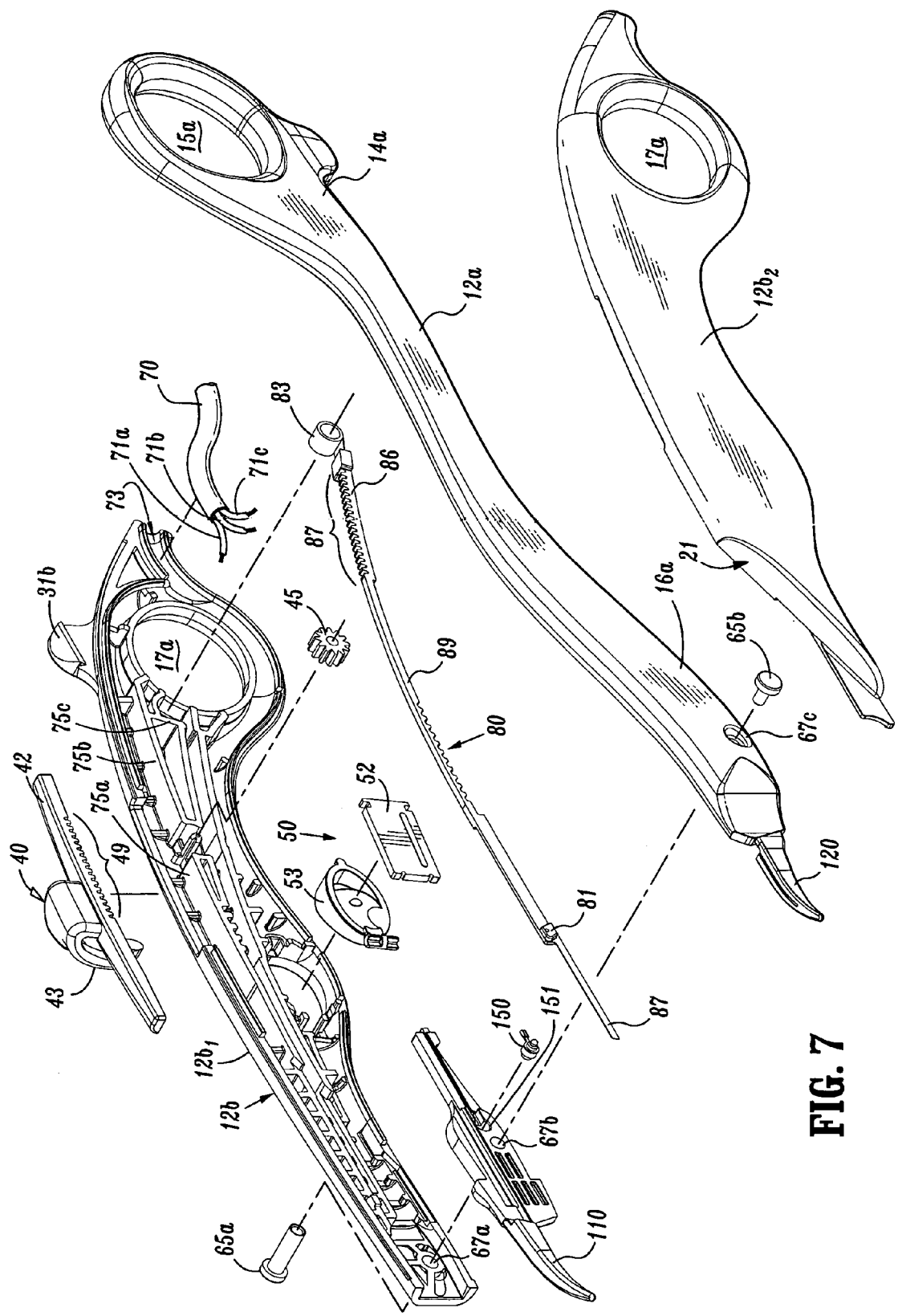
FIG. 7 is a perspective view of the forceps of FIG. 1 with parts separated.
Figure 8:
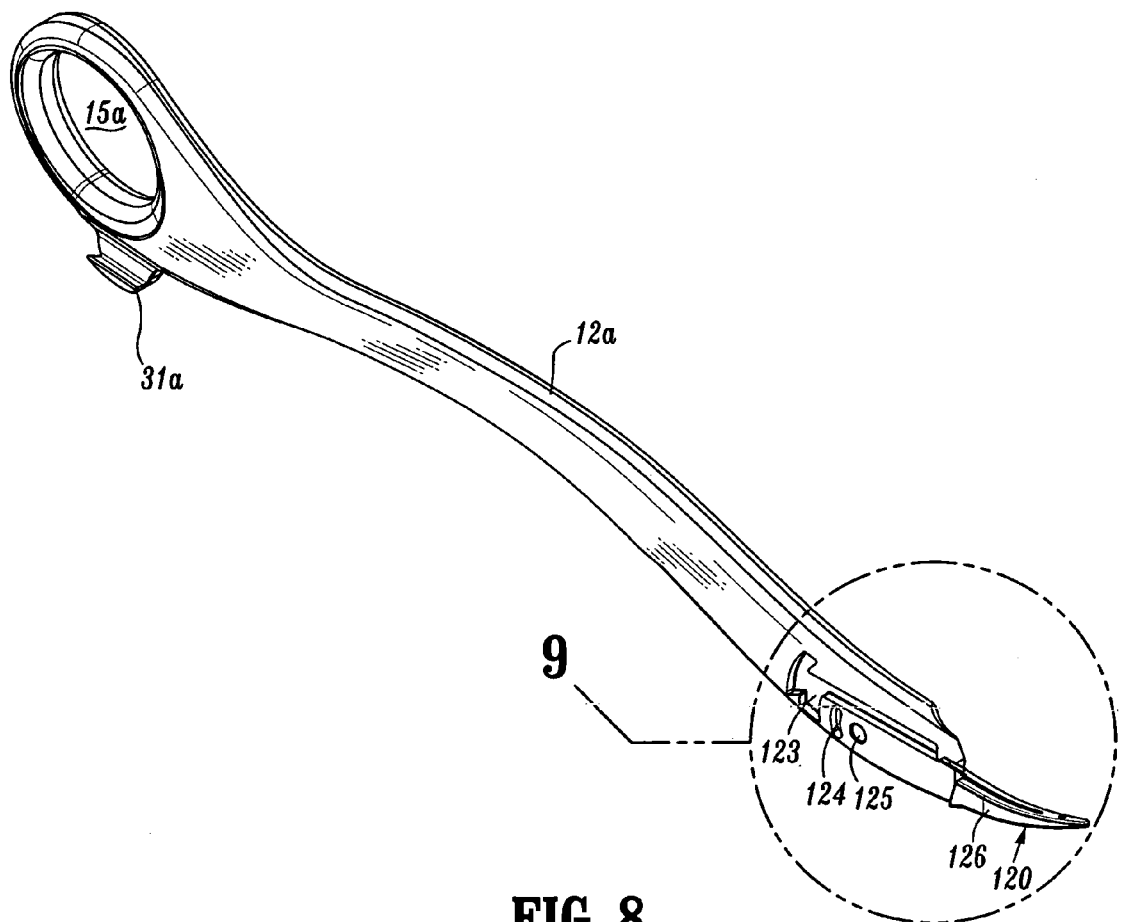
FIG. 8 is a perspective view of one shaft of the forceps of FIG. 1.

As best seen in FIG. 7, shaft 12b is constructed from two components, namely, 12b1 and 12b2, which matingly engage one another about the distal end 16a of shaft 12a to form shaft 12b. It is envisioned that the two component halves 12b1 and 12b2 may be ultrasonically-welded together at a plurality of different weld points or the component halves 12b1 and 12b2 may be mechanically engaged in any other known fashion, snap-fit, glued, screwed, etc. After component halves 12b1 and 12b2 are welded together to form shaft 12b, shaft 12a is secured about pivot 65 and positioned within a cut-out or relief 21 defined within shaft portion 12b2 such that shaft 12a is movable relative to shaft 12b. More particularly, when the user moves the shaft 12a relative to shaft 12b to close or open the jaw members 110 and 120, the distal portion of shaft 12a moves within cutout 21 formed within portion 12b2. It is envisioned that configuring the two shafts 12a and 12b in the fashion facilitates gripping and reduces the overall size of the forceps 10 which is especially advantageous during surgeries in small cavities.

As best illustrated in FIG. 1, one of the shafts, e.g., 12b, includes a proximal shaft connector 77 which is designed to connect the forceps 10 to a source of electrosurgical energy such as an electrosurgical generator (not shown). The proximal shaft connector 77 electromechanically engages an electrosurgical cable 70 such that the user may selectively apply electrosurgical energy as needed. Alternatively, the cable 70 may be feed directly into shaft 12b.

As explained in more detail below, the distal end of the cable 70 connects to a handswitch 50 to permit the user to selectively apply electrosurgical energy as needed to seal tissue grasped between jaw members 110 and 120. More particularly, the interior of cable 70 houses leads 71a, 71b and 71c which upon activation of the handswitch 50 conduct the different electrical potentials from the electrosurgical generator to the jaw members 110 and 120 (See FIGS. 3 and 4). As can be appreciated, positioning the switch 50 on the forceps 10 gives the user more visual and tactile control over the application of electrosurgical energy. These aspects are explained below with respect to the discussion of the handswitch 50 and the electrical connections associated therewith.

The two opposing jaw members 110 and 120 of the end effector assembly 100 are pivotable about pin 65 from the open position to the closed position for grasping tissue therebetween. Preferably, pivot pin 65 consists of two component halves 65a and 65b which matingly engage and pivotably secure the shafts 12a and 12b during assembly such that the jaw members 110 and 120 are freely pivotable between the open and closed positions. For example, the pivot pin 65 may be configured to be spring loaded such that the pivot snap fits together at assembly to secure the two shafts 12a and 12b for rotation about the pivot pin 65.

The tissue grasping portions of the jaw members 110 and 120 are generally symmetrical and include similar component features which cooperate to permit facile rotation about pivot pin 65 to effect the grasping and sealing of tissue. As a result and unless otherwise noted, jaw member 110 and the operative features associated therewith are initially described herein in detail and the similar component features with respect to jaw member 120 will be briefly summarized thereafter.

Moreover, many of the features of the jaw members 110 and 120 are described in detail in commonly-owned U.S. Patent Application Ser. Nos. 10/284,562, 10/116,824, 09/425,696 (now U.S. Pat. No. 6,511,480), 09/178,027 (now U.S. Pat. No. 6,277,117) and PCT Application Ser. No. PCT/US01/11420 the contents of which are all hereby incorporated by reference in their entirety herein.

Figure 14:
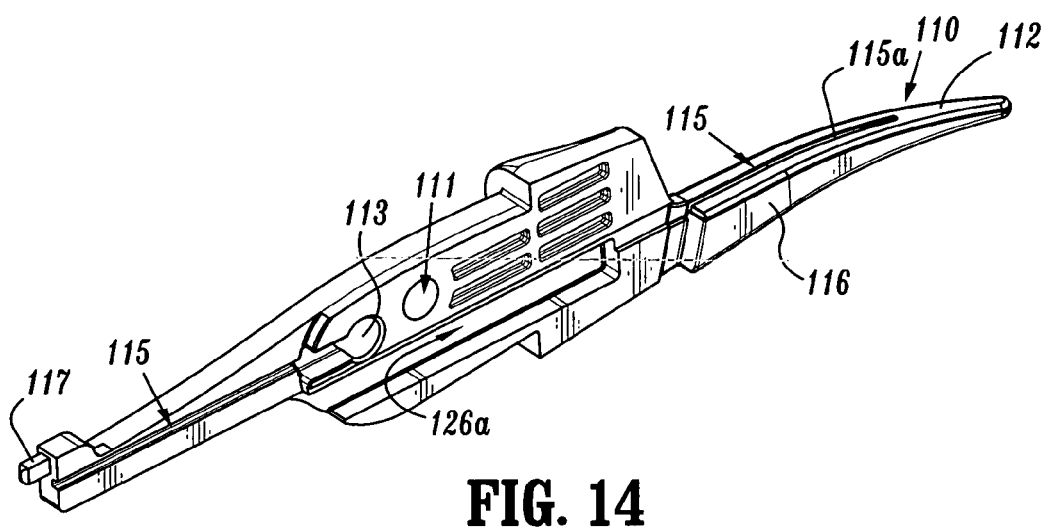
FIG. 14 is an enlarged, left perspective view of the one of the jaw members of the forceps of FIG. 1.
Figure 15:
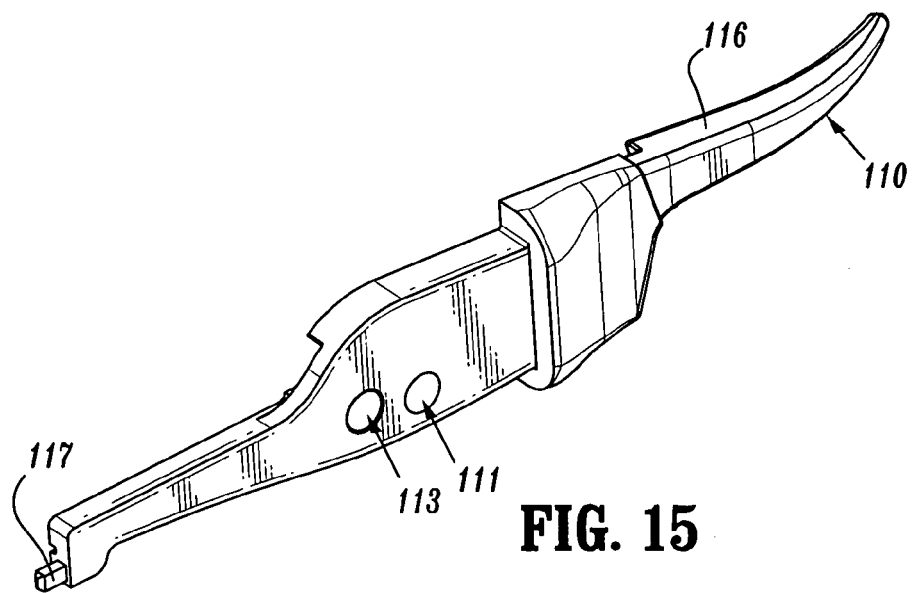
FIG. 15 is an enlarged, right perspective view of the jaw member of FIG. 14.
Figure 16:
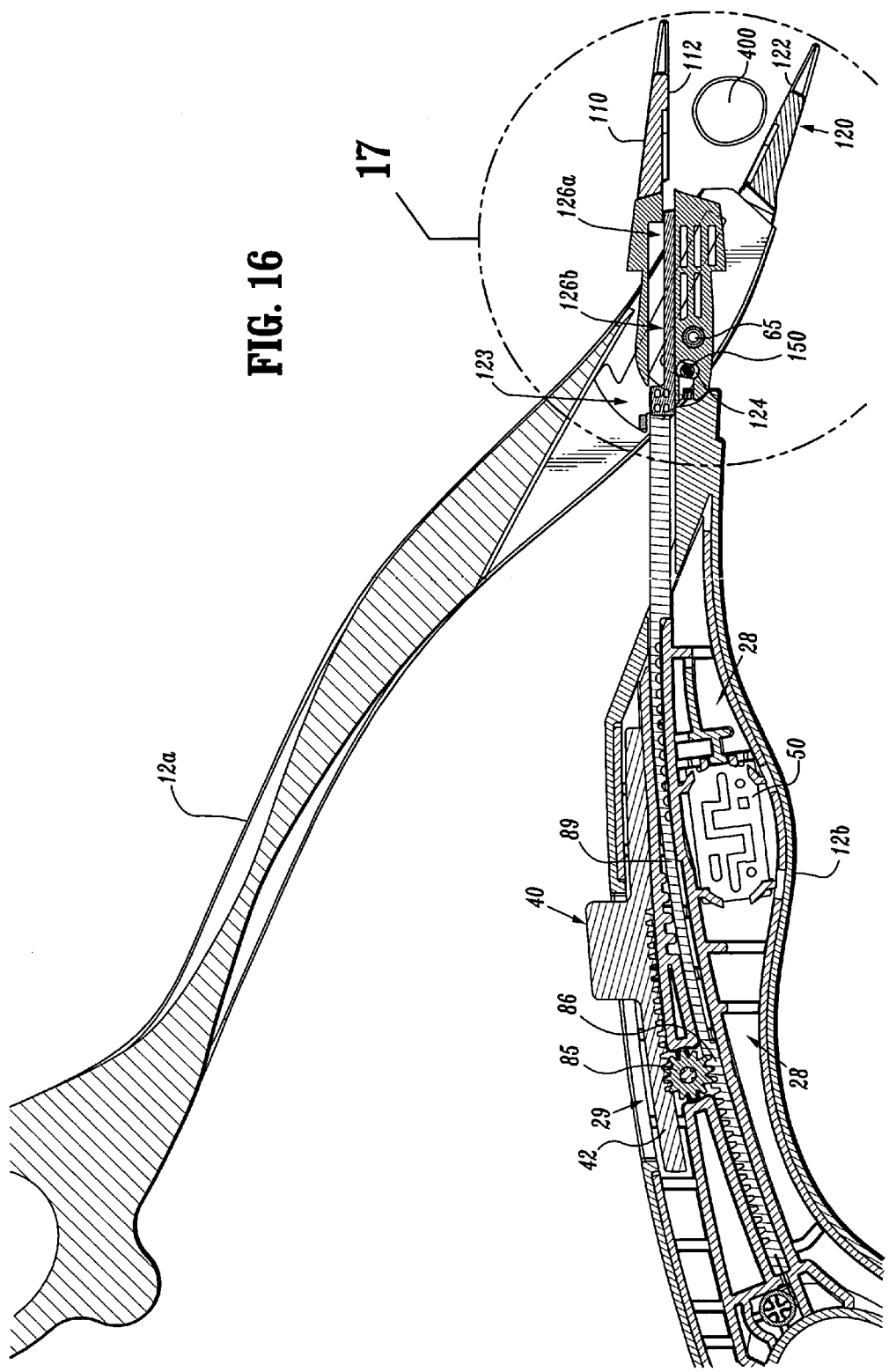
FIG. 16 is side cross sectional view showing the forceps in open configuration for grasping tissue.

As best shown in FIGS. 14 and 15, jaw member 110 includes an insulated outer housing 116 which is dimensioned to mechanically engage an electrically conductive sealing surface 112. The outer insulative housing 116 extends along the entire length of jaw member 110 to reduce alternate or stray current paths during sealing and/or incidental burning of tissue. The electrically conductive surface 112 conducts electrosurgical energy of a first potential to the tissue upon activation of the handswitch 50. Insulated outer housing 116 is dimensioned to securely engage the electrically conductive sealing surface 112. It is envisioned that this may be accomplished by stamping, by overmolding, by overmolding a stamped electrically conductive sealing plate and/or by overmolding a metal injection molded seal plate. Other methods of affixing the seal surface 112 to the outer housing 116 are described in detail in one or more of the above-identified references. Preferably, the jaw members 110 and 120 are made form a conductive material and powder coated with an insulative coating to reduce stray current concentrations during sealing.

It is also contemplated that the electrically conductive sealing surface 112 may include an outer peripheral edge which has a radius and the insulated outer housing 116 meets the electrically conductive sealing surface 112 along an adjoining edge which is generally tangential to the radius and/or meets along the radius. Preferably, at the interface, the electrically conductive surface 112 is raised relative to the insulated outer housing 116. Alternatively, the jaw member 110 including the sealing plate 112 and the outer insulative housing 116 may be formed as part of a molding process to facilitate manufacturing and assembly. These and other envisioned embodiments are discussed in commonly-owned, co-pending PCT application Ser. No. PCT/US01/11412 and commonly owned, co-pending PCT application Ser. No. PCT/US01/11411, the contents of both of these applications being incorporated by reference herein in their entirety.

Preferably, the insulated outer housing 116 and the electrically conductive sealing surface 112 are dimensioned to limit and/or reduce many of the known undesirable effects related to tissue sealing, e.g., flashover, thermal spread and stray current dissipation. All of the aforementioned and cross referenced manufacturing techniques produce an electrode having an electrically conductive surface 112 which is substantially surrounded by an insulated outer housing 116.

Likewise, jaw member 120 includes similar elements which include: an outer housing 126 which engages an electrically conductive sealing surface 122. The electrically conducive sealing surface 122 conducts electrosurgical energy of a second potential to the tissue upon activation of the handswitch 50.

Figure 18:
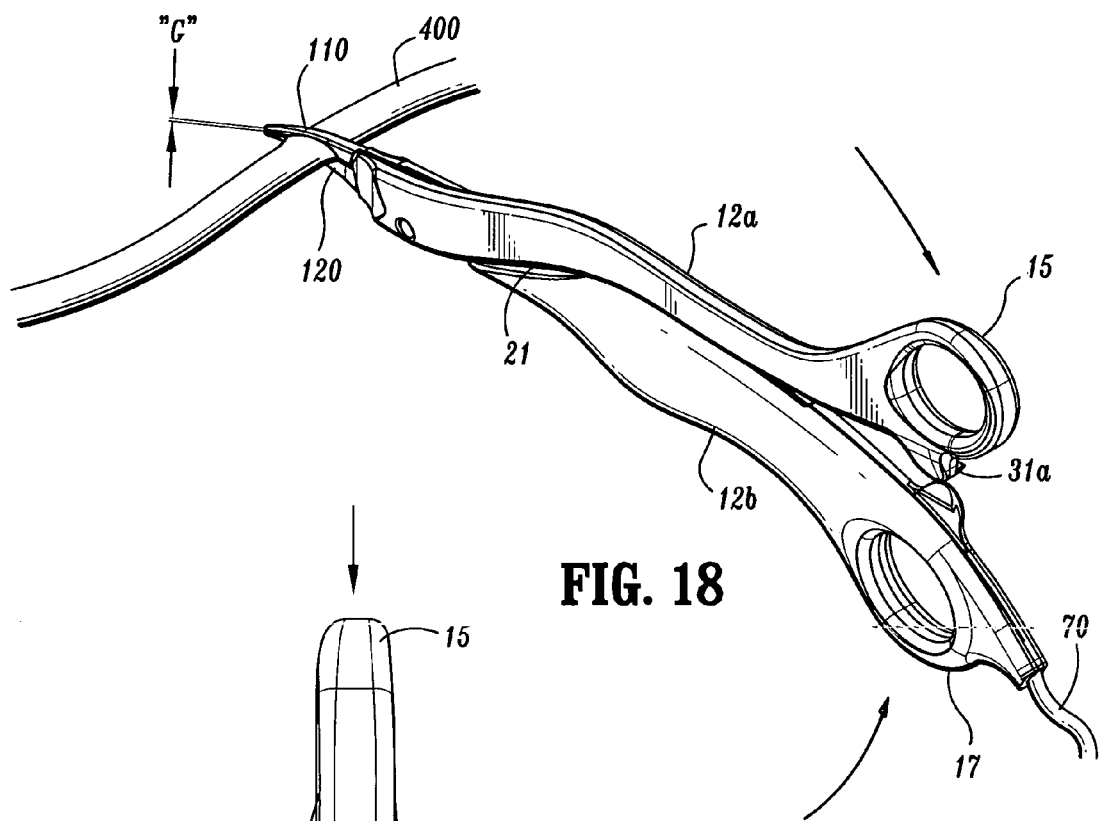
FIG. 18 is a rear, perspective view of the forceps of FIG. 1 shown grasping tissue with a ratchet mechanism shown prior to engagement.
Figure 20:
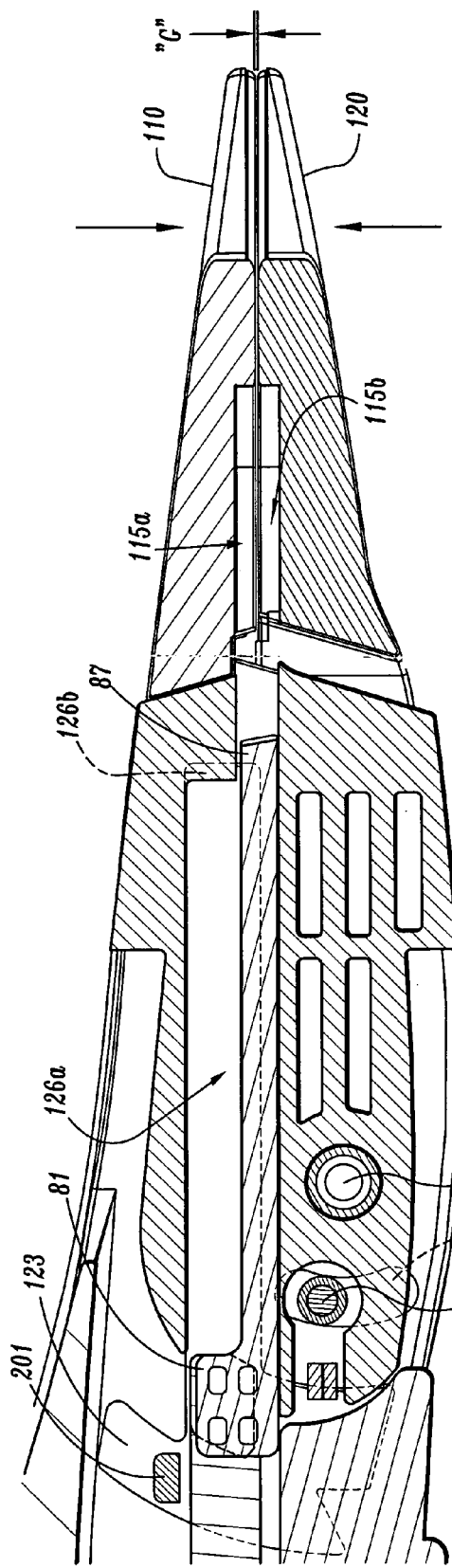
FIG. 20 is a greatly-enlarged, side cross sectional view showing the forceps in a closed position and defining a gap distance "G" between opposing jaw members.

It is envisioned that one of the jaw members, e.g., 120, includes at least one stop member 175 disposed on the inner facing surface of the electrically conductive sealing surface 122 (and/or 112). Alternatively or in addition, the stop member 175 may be positioned adjacent to the electrically conductive sealing surfaces 112, 122 or proximate the pivot pin 65. The stop member(s) is preferably designed to facilitate gripping and manipulation of tissue and to define a gap "G" between opposing jaw members 110 and 120 during sealing (See FIGS. 18 and 20). Preferably the separation distance during sealing or the gap distance "G" is within the range of about 0.001 inches (~0.03 millimeters) to about 0.006 inches (~0.016 millimeters).

A detailed discussion of these and other envisioned stop members 175 as well as various manufacturing and assembling processes for attaching, disposing, depositing and/or affixing the stop members to the electrically conductive sealing surfaces 112, 122 are described in commonly-assigned, co-pending PCT application Ser. No. PCT/US01/11222 which is hereby incorporated by reference in its entirety herein.

As mentioned above, two mechanical factors play an important role in determining the resulting thickness of the sealed tissue and effectiveness of the seal, i.e., the pressure applied between opposing jaw members 110 and 120 and the gap "G" between the opposing jaw members 110 and 120 (or opposing seal surfaces 112 and 122 during activation). It is known that the thickness of the resulting tissue seal cannot be adequately controlled by force alone. In other words, too much force and the sealing surfaces 112 and 122 of the two jaw members 110 and 120 would touch and possibly short resulting in little energy traveling through the tissue thus resulting in a bad seal. Too little force and the seal would be too thick. Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

Preferably, the seal surfaces 112 and 122 are relatively flat to avoid current concentrations at sharp edges and to avoid arcing between high points. In addition and due to the reaction force of the tissue when engaged, jaw members 110 and 120 are preferably manufactured to resist bending, i.e., tapered along their length which provides a constant pressure for a constant tissue thickness at parallel and the thicker proximal portion of the jaw members 110 and 120 will resist bending due to the reaction force of the tissue.

Figure 9:
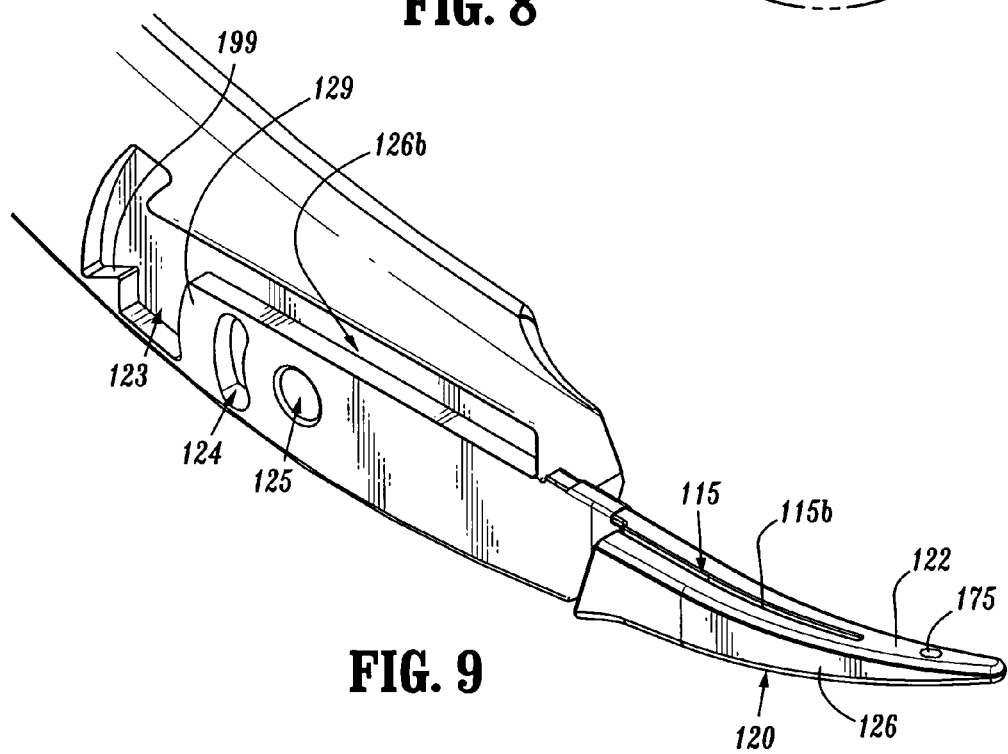
FIG. 9 is an enlarged, perspective view showing the area of detail in FIG. 8.
Figure 13:
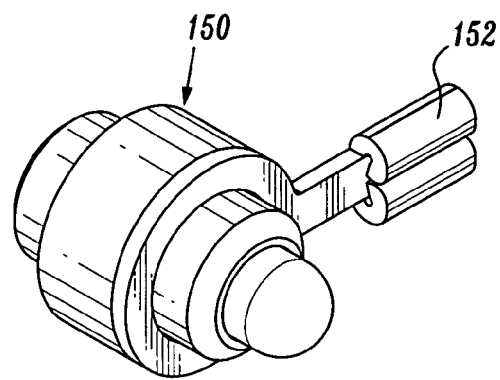
FIG. 13 is a greatly-enlarged perspective view of a distal electrical connector of the forceps of FIG. 1.

As best seen in FIGS. 9 and 14, the jaw members 110 and 120 include a knife channel 115 disposed therebetween which is configured to allow reciprocation of a cutting mechanism 80 therewithin. One example of a knife channel is disclosed in commonly-owned U.S. patent application Ser. No. 10/284,562 the entire contents of which are hereby incorporated by reference herein. Preferably, the complete knife channel 115 is formed when two opposing channel halves 115*a* and 115*b* associated with respective jaw members 110 and 120 come together upon grasping of the tissue. It is envisioned that the knife channel 115 may be tapered or some other configuration which facilitates or enhances cutting of the tissue during reciprocation of the cutting mechanism 80 in the distal direction. Moreover, the knife channel 115 may be formed with one or more safety features which prevent the cutting mechanism 80 from advancing through the tissue until the jaw members 110 and 120 are closed about the tissue.

The arrangement of shaft 12*b* is slightly different from shaft 12*a*. More particularly, shaft 12*b* is generally hollow to define a chamber 28 therethrough which is dimensioned to house the handswitch 50 (and the electrical components associated therewith), the actuating mechanism 40 and the cutting mechanism 80. As best seen in FIGS. 3, 4 and 7, the actuating mechanism 40 includes a rack and pinion system having first and second gear tracks 42 and 86, respectively, and a pinion to advance the cutting mechanism 80. More particularly, the actuating mechanism 40 includes a trigger or finger tab 43 which is operatively associated with a first gear rack 42 such that movement of the trigger or finger tab 43 moves the first rack 42 in a corresponding direction. The actuating mechanism 40 mechanically cooperates with a second gear rack 86 which is operatively associated with a drive rod 89 and which advances the entire cutting mechanism 80 as will be explained in more detail below. Drive rod 89 includes a distal end 81 which is configured to mechanically support the cutting blade 87 and which acts as part of a safety lockout mechanism as explained in more detail below.

Figure 23:
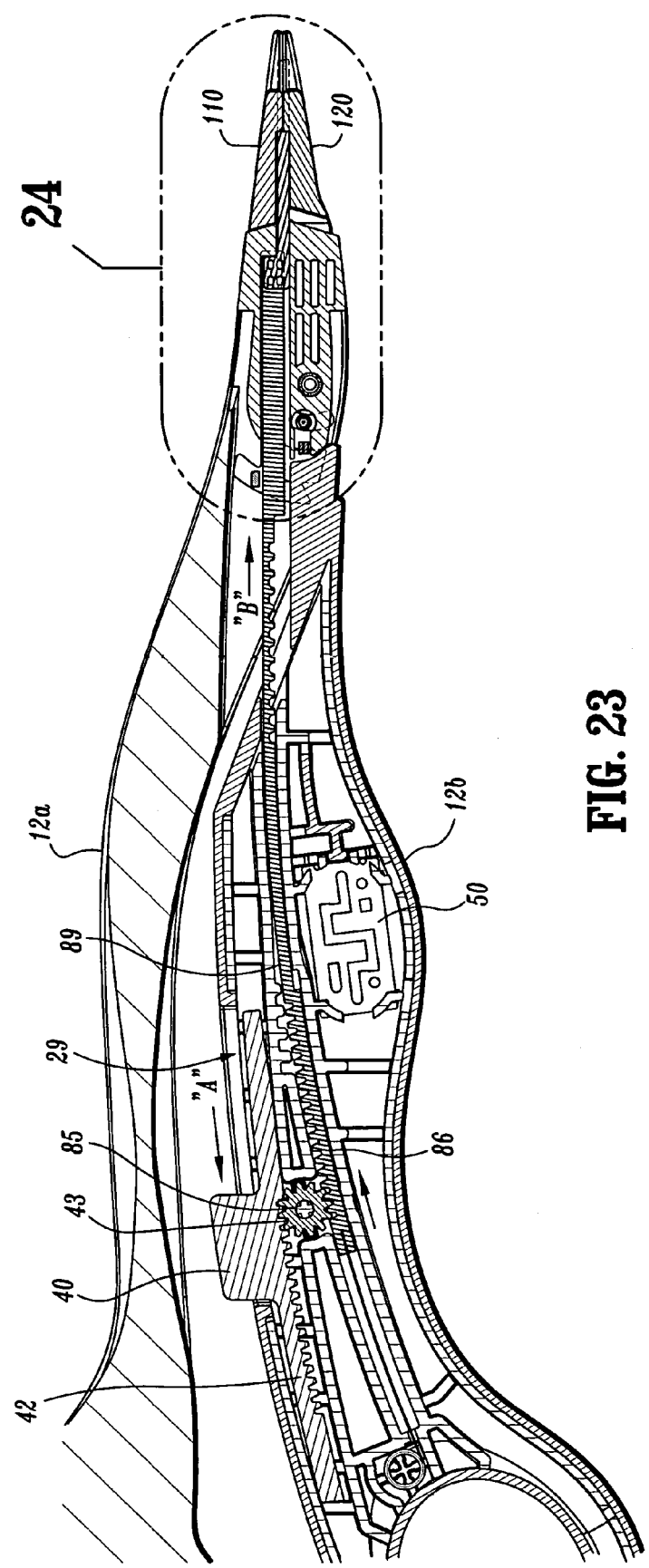
FIG. 23 is a side cross sectional view showing the forceps in a closed position and showing the activation and advancement of the cutting mechanism.

Interdisposed between the first and second gear racks 42 and 86, respectively, is a pinion gear 45 which mechanically meshes with both gear racks 42 and 86 and converts proximal motion of the trigger 43 into distal translation of the drive rod 89 and vice versa. More particularly, when the user pulls the trigger 43 in a proximal direction within a predisposed channel 29 in the shaft 12*b* (See arrow "A" in FIG. 23), the first rack 42 is translated proximally which, in turn, rotates the pinion gear 45 in a counter-clockwise direction. Rotation of the pinion gear 45 in a counter-clockwise direction forces the second rack 86 to translate the drive rod 89 distally (See arrow "B" in FIG. 23) which advances the blade 87 of the cutting mechanism 80 through tissue 400 grasped between jaw members 110 and 120, i.e., the cutting mechanism 80, e.g., knife, blade, wire, etc., is advanced through channel 115 upon distal translation of the drive rod 89.

It is envisioned that multiple gears or gears with different gear ratios may be employed to reduce surgical fatigue which may be associated with advancing the cutting mechanism 80. In addition, it is contemplated the gear tracks 42 and 86 are configured to include a plurality of gear teeth tracks 43 and 87, respectively, which may be of different length to provide additional mechanical advantage for advancing the jaw members 110 and 120 through tissue. The rack and pinion arrangement may be curved for spatial purposes and to facilitate handling and/or to enhance the overall ergonomics of the forceps 10.

A spring 83 may be employed within chamber 28 to bias the first rack 42 upon proximal movement thereof such that upon release of the trigger 43, the force of the spring 83 automatically returns the first rack 42 to its distal most position within channel 29. Obviously, spring 83 may be operatively connected to bias the second rack 86 to achieve the same purpose.

Preferably, the trigger 43 includes one or more ergonomically friendly features which enhance the tactile feel and grip for the user to facilitate actuation of the finger tab 43. Such features may include, raised protuberances, rubber inserts, scallops and gripping surfaces and the like. In addition, the downward orientation of the trigger 43 is believed to be particularly advantageous since this orientation tends to minimize accidental or inadvertent activation of the trigger 43 during handling. Moreover, it is contemplated that integrally associating (molding or otherwise forming) the trigger 43 and the gear rack 42 during the manufacturing process minimizes the number of parts which, in turn, simplifies the overall assembly process.

As best seen in FIGS. 5, 9, 10, 11, 12, 17, 20 and 23, a safety lockout mechanism 200 is associated with the actuating assembly 40 and the cutting mechanism 80 to prevent advancement of the cutting mechanism 80 until the jaw members 110 and 120 are positioned and closed about tissue. Other lockout mechanisms and features are described in commonly-owned U.S. Application Ser. No. 10/460,926 (now U.S. Pat. No. 7,156,846), Ser. No. 10/461,550, 10/462, 121 (now U.S. Pat. No. 7,150,097) and U.S. Provisional Application Ser. No. 60/523,387 which are all incorporated by reference herein in their entirety. The safety lockout mechanism includes a series of inter-cooperating elements which work together to prevent unintentional firing of the cutting mechanism 80 when the jaw members 110 and 120 are disposed in the open position.

More particularly, the distal end 81 of the cutting mechanism 80 is dimensioned to reciprocate within a channel 126*b* defined in the proximal end of jaw member 120 when jaw member 110 and 120 are disposed in a closed position (see FIG. 9). The proximal end of channel 126b defines a recess or relieved portion 123 therein which includes a forward stop 129 which abuts and prevents advancement of the distal end 81 of the cutting mechanism 80 when the jaw members 110 and 120 are disposed in the open position (See FIGS. 9 and 17). The proximal portion of jaw member 120 also includes a guide slot 124 defined therethrough which allows a terminal connector 150 or so called "POGO" pin to ride therein upon movement of the jaw members 110 and 120 from the open to closed positions (See FIGS. 17 and 24). In addition, the proximal end includes an aperture 125 defined therethrough which houses the pivot pin 65. Jaw member 110 also includes a channel 126a which aligns with channel 126b when the jaw members 110 and 120 are disposed in the closed position about tissue.

Figure 17:
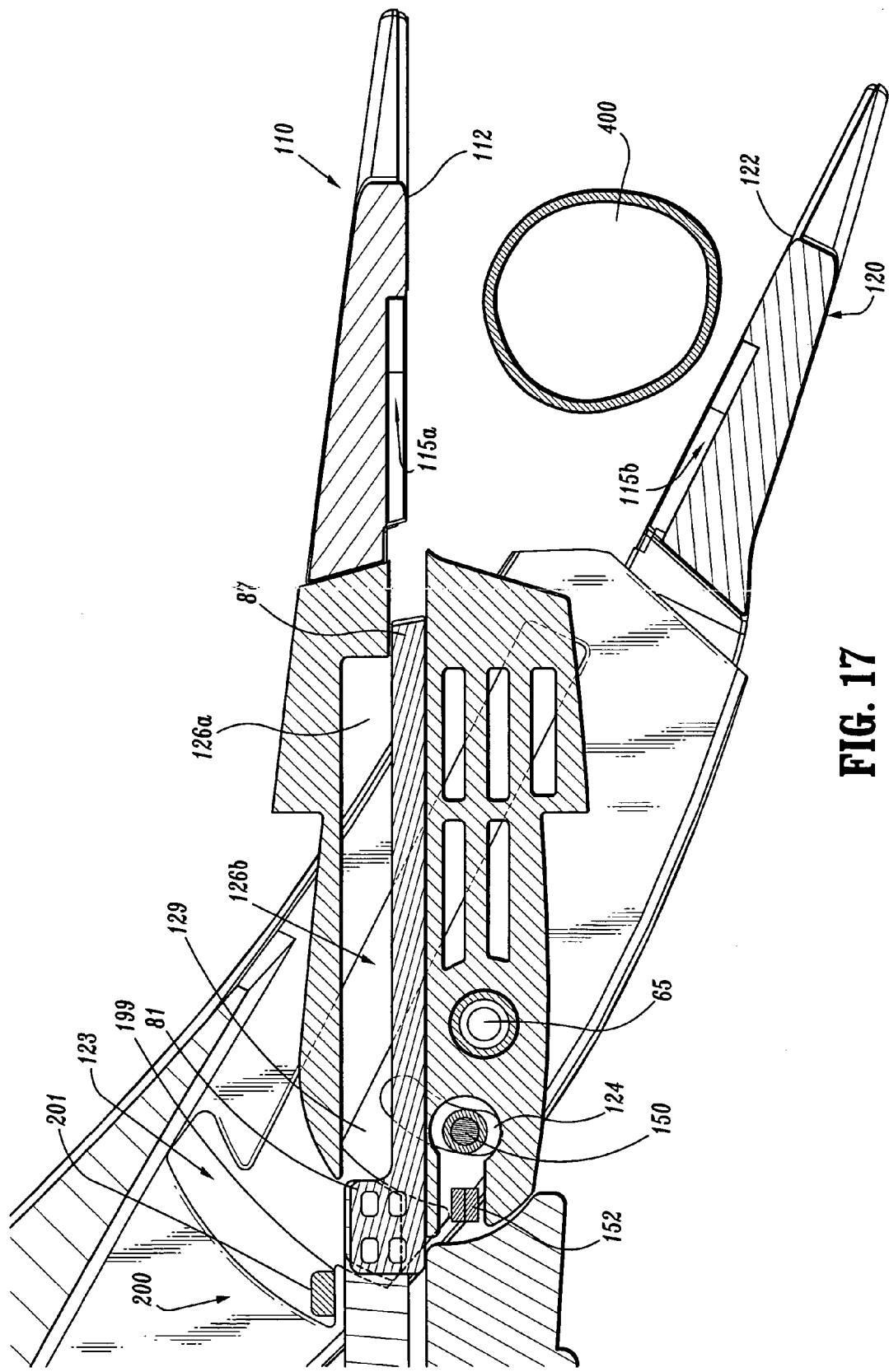
FIG. 17 is a side cross sectional view showing the area of detail in FIG. 16.
Figure 24:
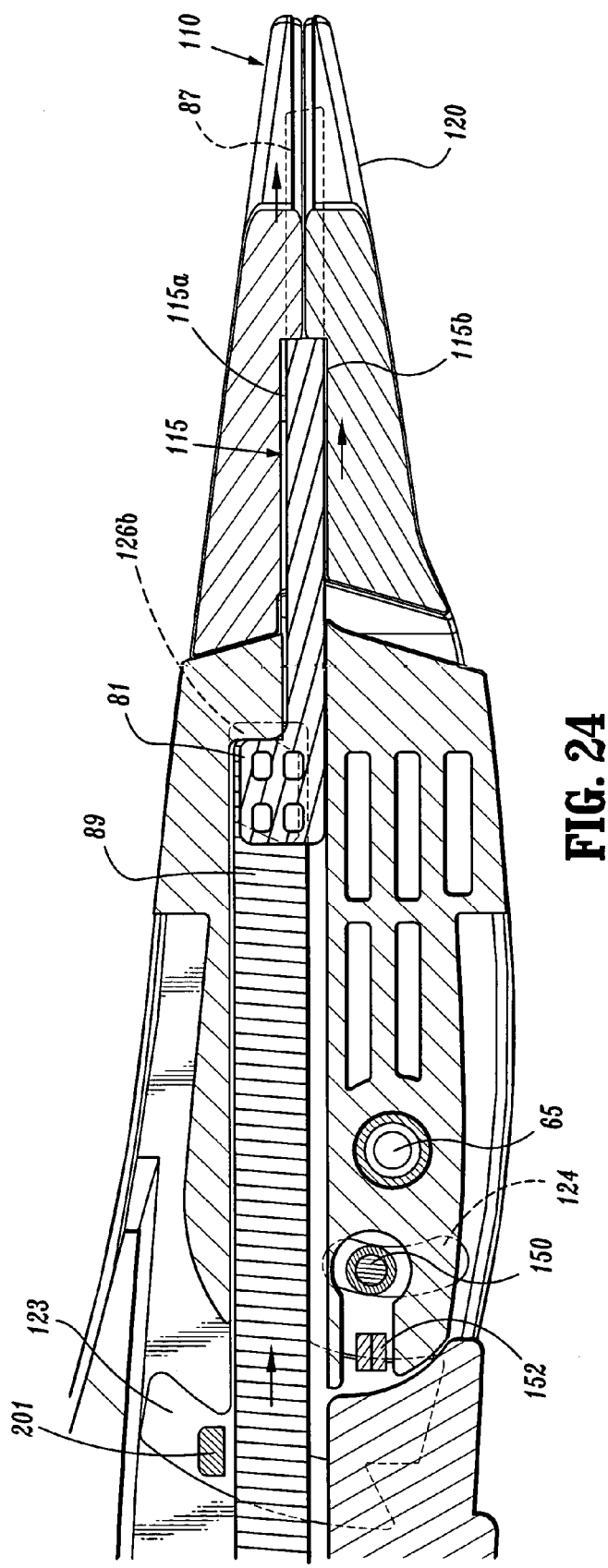
FIG. 24 is an enlarged view of the area of detail in FIG. 24.

As best shown in FIGS. 17 and 24 which show the jaw members 110 and 120 in open and closed orientations, respectively, the operation of the lockout mechanism 200 is easily described. When jaw member 120 is rotated with respect to jaw member 110 about pivot 65 a flanged portion 81a of the distal end 81 of cutting mechanism 80 is slidingly incorporated within recess 123 and against stop 129 located in the proximal end of jaw member 120 (See FIG. 12). The stop 129 prevents the cutting mechanism 80 from moving forward due to unintentional actuation of the trigger 43. At the same time, the terminal connector 150 moves freely within slot 124 upon rotation of the jaw members 110 and 120. It is envisioned that the terminal connector 150 is seated within aperture 151 within jaw member 110 and rides within slot 124 of jaw member 120 to provide a "running" or "brush" contact to supply electrosurgical energy to jaw member 120 during the pivoting motion of the forceps 10 (See FIG. 17). Recess 123 also includes a rim or flange 199 which prevents over-rotation of shaft 12a relative to shaft 12b. More particularly and as best seen on FIGS. 9 and 17, flange 199 is dimensioned to abut a stop 201 disposed within forceps 110 when rotated to a fully open position to prevent unintentional over-rotation of the forceps 10.

When the jaw members 110 and 120 are moved to the closed position as illustrated in FIG. 24, the safety lockout mechanism 200 automatically disengages to allow distal advancement of the cutting mechanism 80. More particularly, when the jaw members 110 and 120 are closed about tissue, the distal end 81 including the flanged portion 81a automatically aligns within the channels 126a and 126 of jaw members 110 and 120, respectively, to allow selective actuation of the cutting mechanism 80. As shown in FIG. 24, the distal end 81 advances through channel 126a and 126b forcing the knife blade 87 through knife channel 115 (115a and 115b) to cut tissue. As described above, when the actuating flange 43 is released, spring 83 biases the drive rod 89 back to the proximal-most position (not shown) which, in turn, re-aligns distal end 81 with recess 123 to allow the jaw members 110 and 120 to be moved to the open position to release the tissue 400.

It is envisioned that the safety lockout mechanism 200 may include one or more electrical or electromechanical sensors (not shown) which prevent the cutting mechanism 80 from advancing through tissue until a tissue seal has been created. For example, the safety lockout mechanism 200 could include a sensor which upon completion of a tissue seal activates a switch or release (not shown) which unlocks the cutting mechanism 80 for advancement through tissue.

As best seen in FIGS. 9 and 10, blade 87 is flexible so it easily advances through the curved knife channel 115. For example, upon distal advancement of the cutting mechanism 80, the cutting blade 87 will simply flex and ride around the knife channel 115 through the tissue 400 held between jaw members 110 and 120. A curved blade (not shown) may also be utilized which has a similar radius of curvature as the knife channel 115 such that the blade will travel through the knife channel 115 without contacting the surfaces of the knife channel 115.

Figure 2:
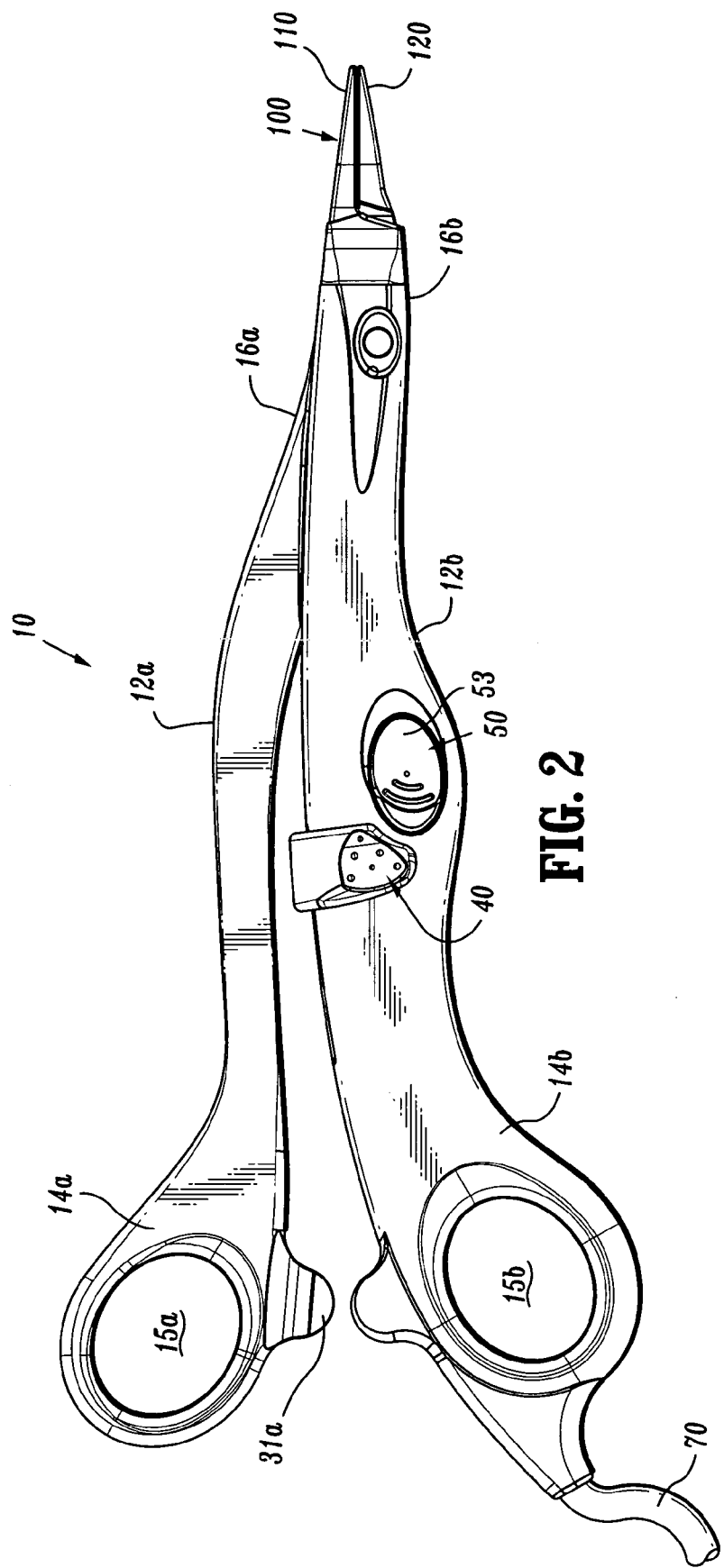
FIG. 2 is a left, side view of the forceps of FIG. 1.
Figure 5:
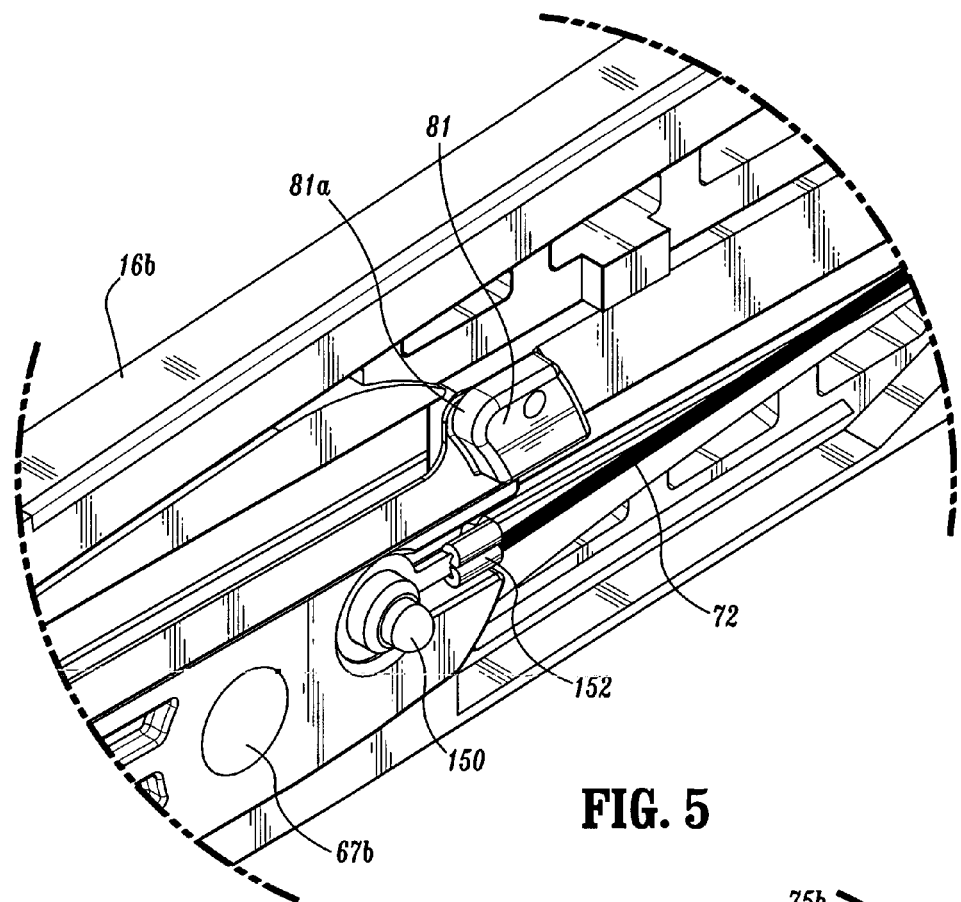
FIG. 5 is an enlarged, perspective view showing the area of detail in FIG. 3.
Figure 6:
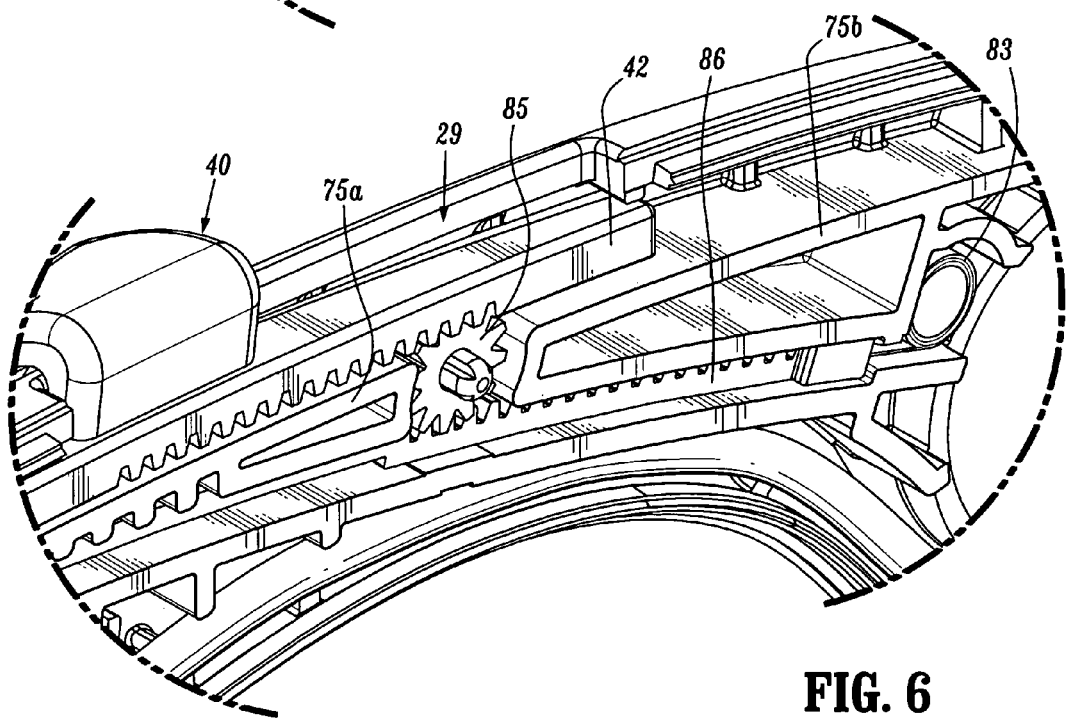
FIG. 6 is an enlarged, perspective view showing the area of detail in FIG. 3.
Figure 19:
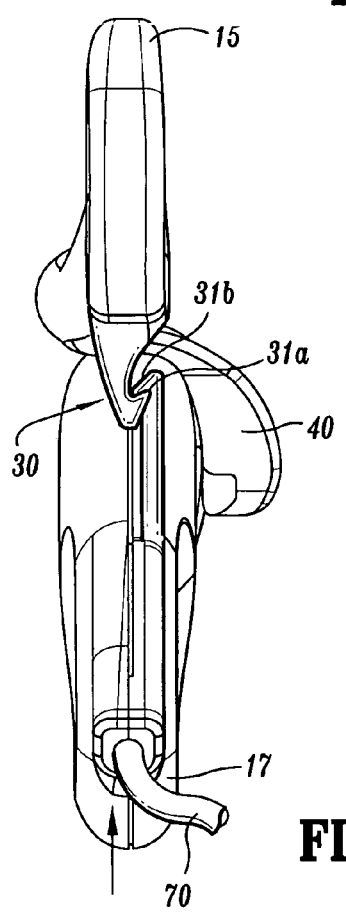
FIG. 19 is a rear view of the forceps of FIG. 1 showing the ratchet mechanism engaged.

FIGS. 1, 2 and 19 show a ratchet 30 for selectively locking the jaw members 110 and 120 relative to one another in at least one position during pivoting. A first ratchet interface 31a extends from the proximal end 14a of shaft member 12a towards a second ratchet interface 31b on the proximal end 14b of shaft 12b in general vertical registration therewith such that the inner facing surfaces of each ratchet 31a and 31b abut one another upon closure of the jaw members 110 and 120 about the tissue 400. It is envisioned that each ratchet interface 31a and 31b may include a plurality of step-like flanges (not shown) which project from the inner facing surface of each ratchet interface 31a and 31b such that the ratchet interfaces 31a and 31b interlock in at least one position. Preferably, each position associated with the cooperating ratchet interfaces 31a and 31b holds a specific, i.e., constant, strain energy in the shaft members 12a and 12b which, in turn, transmits a specific closing force to the jaw members 110 and 120. It is envisioned that the ratchet 30 may include graduations or other visual markings which enable the user to easily and quickly ascertain and control the amount of closure force desired between the jaw members. It is envisioned that the shafts 12a and 12b may be manufactured from a particular plastic material which is tuned to apply a particular closure pressure within the above-specified working range to the jaw members 110 and 120 when ratcheted. As can be appreciated, this simplified the manufacturing process and eliminates under pressurizing and over pressurizing the jaw member s 110 and 120 during the sealing process. The proximal connector 77 may include a stop or protrusion 63 (See FIG. 7) which prevents the user from over pressurizing the jaw members 110 and 120 by squeezing the handle 15 and 17 beyond the ratchet positions.

It is envisioned that by making the forceps 10 disposable, the forceps 10 is less likely to become damaged since it is only intended for a single use and, therefore, does not require cleaning or re-sterilization. As a result, the functionality and consistency of the vital sealing components, e.g., the conductive surfaces 112 and 122, the stop member(s) 175, and the insulative housings 126 and 116 will assure a uniform and quality seal.

FIGS. 3 and 4 show the electrical details relating to the switch 50. More particularly and as mentioned above, cable 70 includes three electrical leads 71a, 71b and 71c which are fed through shaft 12b. The electrosurgical cable 70 is fed into the bottom of shaft 12b and is held securely therein by one or more mechanical interfaces (not shown). Lead 71c extends directly from cable 70 and connects to jaw member 120 to conduct the second electrical potential thereto. Leads 71a and 71b extend from cable 70 and connect to a circuit board 52.

Several different types of handswitches 50 are envisioned, for example, switch 50 is a regular push-button style switch but may be configured more like a toggle switch which permits the user to selectively activate the forceps 10 in a variety of different orientations, i.e., multi-oriented activation, which simplifies activation.

One particular type of handswitch is disclosed in commonly-owned, co-pending U.S. patent application Ser. No. 10/460,926 (now U.S. Pat. No. 7,156,846), the contents of which are hereby incorporated by reference herein.

The electrical leads 71a and 71b are electrically connected to the circuit board 52 such that when the switch 50 is depressed, a trigger lead 72 carries the first electrical potential from the circuit board 52 to jaw member 110. As mentioned above, the second electrical potential is carried by lead 71c directly from the generator (not shown) to jaw member 120 through the terminal connector 150 as described above. It is envisioned that a safety switch or circuit (not shown) may be employed such that the switch 50 cannot fire unless the jaw members 110 and 120 are closed and/or unless the jaw members 110 and 120 have tissue 400 held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions.

Various sensor mechanisms and feedback systems are described in commonly-owned, co-pending U.S. patent application Ser. No. 10/427,832 (now U.S. Pat. No. 7,137,980), the entire contents of which are hereby incorporated by reference herein.

As best shown in FIGS. 1, 2 and 7, a switch cap 53 is positioned in electromechanical communication with the circuit board 52 along one side of shaft 12b to facilitate activation of switch 50. As can be appreciated, the position of the switch cap 53 enables the user to easily and selectively energize the jaw members 110 and 120 with a single hand. It is envisioned that the switch cap 53 may be hermetically-sealed to avoid damage to the circuit board 52 during wet operating conditions. In addition, it is contemplated that by positioning the switch cap 53 at a point distal to the actuating assembly 40, the overall sealing process is greatly simplified and ergonomically advantageous to the surgeon, i.e., after activation, the surgeon's finger is automatically poised for actuation of the actuating assembly 40 to advance the cutting mechanism 80. The geometry also disallows inadvertent actuation of the forceps 10 when the forceps 10 is not activated or "powered down".

The jaw members 110 and 120 are electrically isolated from one another such that electrosurgical energy can be effectively transferred through the tissue to form a tissue seal. Preferably, each jaw member, e.g., 110, includes a uniquely-designed electrosurgical cable path disposed therethrough which transmits electrosurgical energy to the electrically conductive sealing surface 112. It is envisioned that the jaw members 110 and 120 may include one or more cable guides or crimp-like electrical connectors to direct the cable leads towards electrically conductive sealing surfaces 112 and 122. Preferably, cable leads are held securely along the cable path to permit pivoting of the jaw members 110 and 120 about pivot 65.

As best shown in FIG. 7, the cable leads 71a, 71b and 71c are protected by two insulative layers, an outer protective sheath which surrounds all three leads 71a, 71b and 71c and a secondary protective sheath which surrounds each individual cable lead, 71a, 71b and 71c, respectively. The two electrical potentials are isolated from one another by virtue of the insulative sheathing surrounding each cable lead 71a, 71b and 71c.

Figure 21:
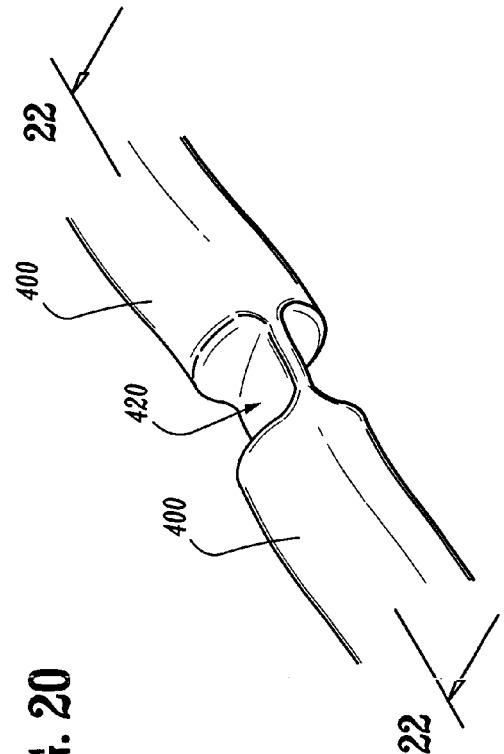
FIG. 21 is a greatly-enlarged, perspective view of a tissue seal.
Figure 22:
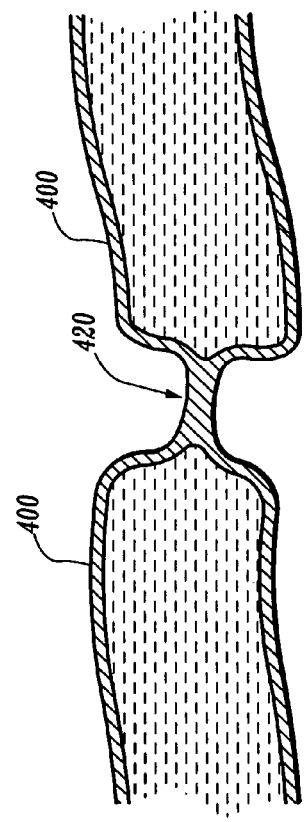
FIG. 22 is a side cross sectional view taken along line 22-22 of FIG. 21.
Figure 25:
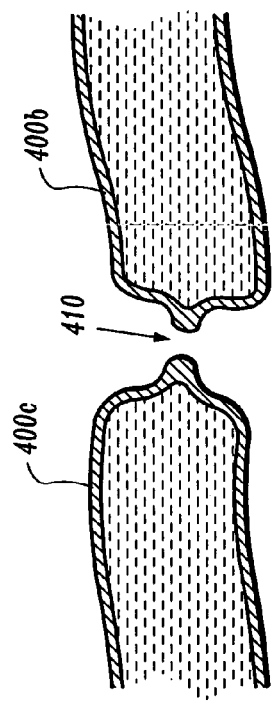
FIG. 25 is a greatly-enlarged, cross sectional view showing tissue separated along the tissue seal after advancement of the cutting mechanism.

In operation, the surgeon simply utilizes the two opposing handle members 15 and 17 to grasp tissue between jaw members 110 and 120. The surgeon then activates the handswitch 50 to provide electrosurgical energy to each jaw member 110 and 120 to communicate energy through the tissue held therebetween to effect a tissue seal (See FIGS. 21 and 22). Once sealed, the surgeon activates the actuating mechanism 40 to advance the cutting blade 87 through the tissue to sever the tissue 400 along the tissue seal (See FIG. 25).

From the foregoing and with reference to the various figure drawings, those skilled in the art will appreciate that certain modifications can also be made to the present disclosure without departing from the scope of the same. For example, although the electrical connections are preferably incorporated within one shaft 12b and the forceps 10 is intended for right-handed use, it is contemplated the electrical connections may be incorporated within the other shaft 12a depending upon a particular purpose and/or to facilitate manipulation by a left-handed user. Alternatively, the forceps 10 may operated in an upside down orientation for left-handed users without compromising or restricting any operating characteristics of the forceps 10.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120.

Commonly-owned U.S. patent application Ser. No. 10/427,832 (now U.S. Pat. No. 7,137,980) discloses several different types of sensory feedback mechanisms and algorithms which may be utilized for this purpose.

Experimental results suggest that the magnitude of pressure exerted on the tissue by the sealing surfaces of the jaw members 110 and 120 is important in assuring a proper surgical outcome. Tissue pressures within a working range of about 3 kg/cm$^2$ to about 16 kg/cm$^2$ and, preferably, within a working range of 7 kg/cm$^2$ to 13 kg/cm$^2$ have been shown to be effective for sealing arteries and vascular bundles. Tissue pressures within the range of about 4 kg/cm$^2$ to about 10 kg/cm$^2$ have proven to be particularly effective in sealing arteries and tissue bundles. Preferably, the inter-engaging surfaces 31a and 31b of the ratchet 30 are positioned to provide a closure within this working range. In addition and if the ratchet 30 includes multiple positions as explained above, it is envisioned that each particular ratchet position employs a specific closure force on tissue for particular surgical purposes. For example, the shafts 12a and 12b may be manufactured such that the spring constants of the shaft portions 12a and 12b, in conjunction with the placement of the ratchet interfaces 31a and 31b, will yield pressures within the above working range. The successive positions of the ratchet interfaces 21a and 31b (and any other positions as described above) increase the closure force between opposing sealing surfaces 112 and 122 incrementally within the above working range.

It is also envisioned that the drive rod 89 may be connected to the same or alternate source of electrosurgical energy and may be selectively energizable by the surgeon during cutting. As can be appreciated, this would enable the surgeon to electrosurgically cut the tissue along the tissue seal. As a result thereof, a substantially dull blade may be employed to electrosurgically cut the tissue. It is also envisioned that a substantially dull blade may be utilized with a spring loaded cutting mechanism which, due to the clamping pressure between the opposing jaw members 110 and 120 and due to the force at which the spring-loaded cutting mechanism advances the blade, the tissue will sever along the tissue seal.

It is also contemplated that the forceps may include a safety blade return mechanism (not shown). For example and as mentioned above, the cutting blade 80 may include one or more springs which automatically return the cutting blade 87 after actuation of the actuator 40. In addition, a manual return may be included which allows the user to manually return the blade 87 if the automatic blade return (e.g., spring) should fail due to sticking, skewing, or some other unforeseen surgical condition. Alternatively, the actuating mechanism 40 may be spring-loaded and advanced automatically when tab 43 is depressed by the surgeon. After deployment, the surgeon manually retracts the switch 43 to reset the switch 43 and cutting mechanism 80 for subsequent deployment.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An open electrosurgical forceps for sealing tissue, comprising:
    a pair of first and second shaft members each having a jaw member disposed at a distal end thereof, the jaw members being movable from a first position in spaced relation relative to one another to at least one subsequent position wherein the jaw members cooperate to grasp tissue therebetween;
    each of the jaw members including an electrically conductive sealing plate for communicating electrosurgical energy through tissue held therebetween;
    at least one of the jaw members including a knife channel defined along a length thereof, the knife channel being dimensioned to reciprocate a cutting mechanism therealong;
    an actuator for selectively advancing the cutting mechanism from a first position wherein the cutting mechanism is disposed proximal to tissue held between the jaw members to at least one subsequent position wherein the cutting mechanism is disposed distal to tissue held between the jaw members, the actuator including a trigger which cooperates with a rack and pinion system to advance the cutting mechanism between its first and second positions; and
    wherein the rack and pinion system includes a first gear-like rack in mechanical cooperation with the trigger, a second gear-like rack in mechanical cooperation with the cutting mechanism, and a pinion rotatable about an axis disposed between the first and second gear-like racks.

2. An open electrosurgical forceps for sealing tissue according to claim 1 wherein the rack and pinion system is disposed within one of the first and second shaft members.

3. An open electrosurgical forceps for sealing tissue according to claim 1 wherein the trigger of the actuator is pulled proximally to actuate the rack and pinion system to distally advance the cutting mechanism through the cutting slot.

4. An open electrosurgical forceps for sealing tissue according to claim 1 wherein the trigger of the actuator is pulled proximally to proximally move the first rack and to distally advance the second rack.

5. An open electrosurgical forceps for sealing tissue according to claim 1 further comprising a safety lockout to prevent reciprocation of the cutting mechanism when the jaw members are disposed in the first position.

6. An open electrosurgical forceps for sealing tissue according to claim 5 wherein the safety lockout forms part of at least one of the jaw members.

7. An open electrosurgical forceps for sealing tissue according to claim 5 wherein the safety lockout forms part of the cutting mechanism.

8. An open electrosurgical forceps for sealing tissue according to claim 1 further comprising at least one spring for automatically biasing the cutting mechanism in the first position.

9. An open electrosurgical forceps for sealing tissue according to claim 8 wherein the at least one spring for automatically returning the cutting mechanism back to the first position is mechanically associated with the cutting mechanism.

10. An open electrosurgical forceps for sealing tissue according to claim 1 wherein the first rack is integrally associated with the trigger.

11. An open electrosurgical forceps for sealing tissue according to claim 1 wherein the second rack is integrally associated with the cutting mechanism.

12. An open electrosurgical forceps for sealing tissue according to claim 1, wherein the trigger is proximally and distally translatable along one of the first and second shaft members.

* * * * *